US010052027B2

(12) United States Patent
Tajbakhsh et al.

(10) Patent No.: US 10,052,027 B2
(45) Date of Patent: *Aug. 21, 2018

(54) SYSTEM AND METHOD FOR AUTOMATIC POLYP DETECTION USING GLOBAL GEOMETRIC CONSTRAINTS AND LOCAL INTENSITY VARIATION PATTERNS

(71) Applicants: MAYO FOUNDATION FOR MEDICAL EDUCATION AND RESEARCH, Rochester, MN (US); ARIZONA BOARD OF REGENTS on Behalf of Arizona State University, Scottsdale, AZ (US)

(72) Inventors: Nima Tajbakhsh, Tempe, AZ (US); Jianming Liang, Phoenix, AZ (US); Suryakanth R. Gurudu, Phoenix, AZ (US)

(73) Assignees: Mayo Foundation for Medical Education and Research, Rochester, MN (US); Arizona Board of Regents on behalf of Arizona State University, Scottsdale, AZ (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/617,111

(22) Filed: Jun. 8, 2017

(65) Prior Publication Data
US 2017/0265747 A1   Sep. 21, 2017

Related U.S. Application Data

(63) Continuation of application No. 14/853,682, filed on Sep. 14, 2015, now Pat. No. 9,700,213.
(Continued)

(51) Int. Cl.
*G06K 9/00* (2006.01)
*A61B 5/00* (2006.01)
(Continued)

(52) U.S. Cl.
CPC .......... *A61B 5/0084* (2013.01); *G06K 9/4604* (2013.01); *G06T 7/0012* (2013.01);
(Continued)

(58) Field of Classification Search
USPC ........ 382/100, 103, 106–107, 128–134, 162, 382/168, 173, 181, 199, 203, 209, 219,
(Continued)

(56) References Cited

U.S. PATENT DOCUMENTS 8,184,888 B2 * 5/2012 Lu ........................... G06T 7/143
382/131
8,369,593 B2 * 2/2013 Peng ..................... A61B 6/032
378/21
(Continued)

OTHER PUBLICATIONS

Tajbakhsh, et al., "A classification-enhanced vote accumulation scheme for detecting colonic polyps", Abdominal maging, 2013, vol. 8198 of Lecture Notes in Computer Science, pp. 53-62.*

*Primary Examiner* — Seyed Azarian
(74) *Attorney, Agent, or Firm* — Quarles & Brady LLP

(57) ABSTRACT

A system and methods for polyp detection using optical colonoscopy images are provided. In some aspects, the system includes an input configured to receive a series of optical images, and a processor configured to process the series of optical images with steps comprising of receiving an optical image from the input, constructing an edge map corresponding to the optical image, the edge map comprising a plurality of edge pixel, and generating a refined edge map by applying a classification scheme based on patterns of intensity variation to the plurality of edge pixels in the edge map. The processor may also process the series with steps of identifying polyp candidates using the refined edge map, computing probabilities that identified polyp candidates are polyps, and generating a report, using the computed prob-
(Continued)

abilities, indicating detected polyps. The system also includes an output for displaying the report.

20 Claims, 21 Drawing Sheets

Related U.S. Application Data

(60) Provisional application No. 62/049,901, filed on Sep. 12, 2014.

(51) Int. Cl.
*G06T 7/00* (2017.01)
*G06K 9/46* (2006.01)
*A61B 6/02* (2006.01)

(52) U.S. Cl.
CPC ............... *G06T 2207/10068* (2013.01); *G06T 2207/20081* (2013.01); *G06T 2207/30032* (2013.01)

(58) Field of Classification Search
USPC ....... 382/232, 254, 274, 276, 287, 291, 305, 382/312; 378/4, 21, 41
See application file for complete search history.

(56) References Cited

U.S. PATENT DOCUMENTS

| | | | |
|---|---|---|---|
| 2009/0074272 A1* | 3/2009 | Lu | G06T 7/0012 382/128 |
| 2010/0189326 A1* | 7/2010 | McGinnis | G06T 7/0012 382/131 |
| 2011/0206250 A1* | 8/2011 | McGinnis | G06T 7/0012 382/128 |

* cited by examiner

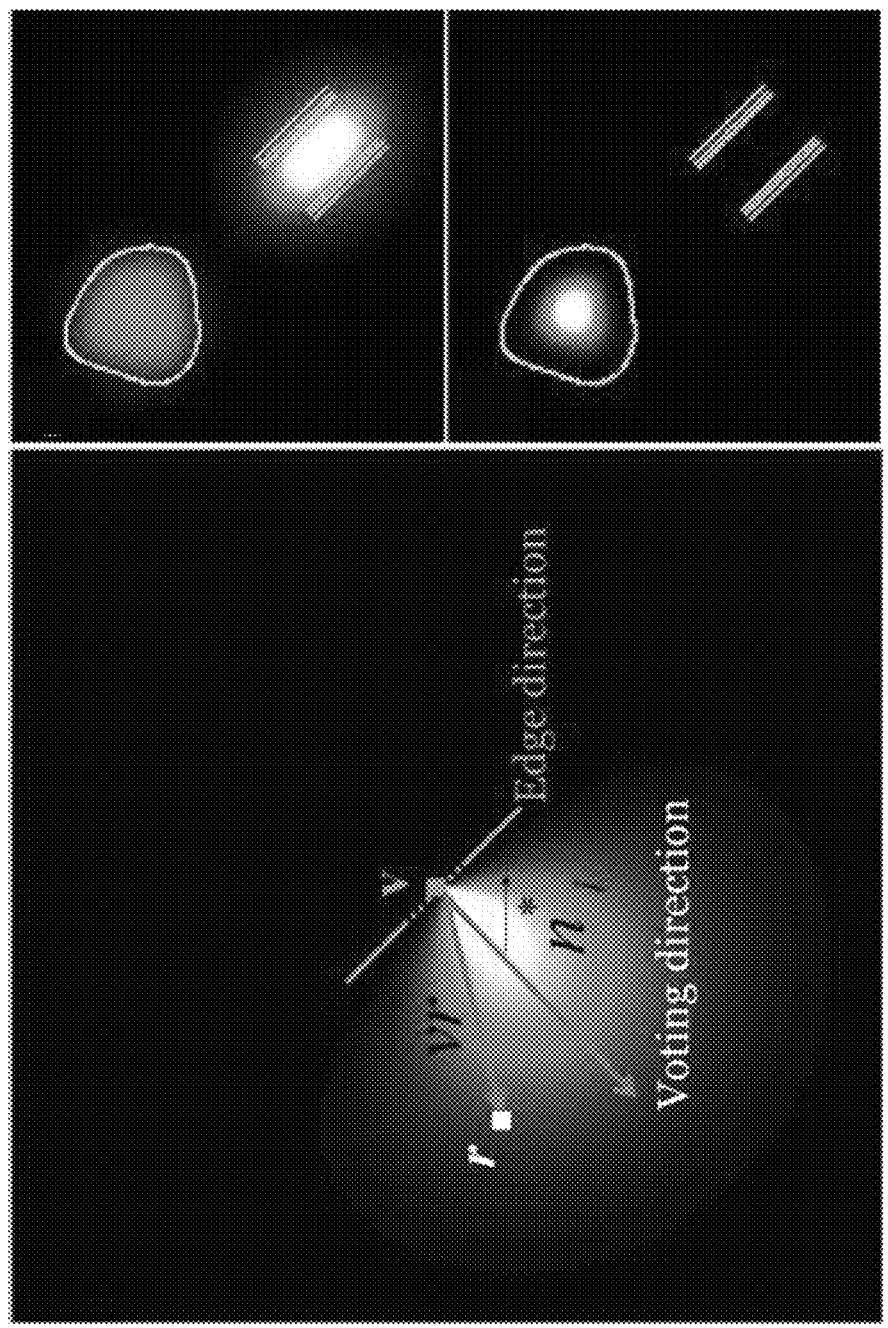

SYSTEM AND METHOD FOR AUTOMATIC POLYP DETECTION USING GLOBAL GEOMETRIC CONSTRAINTS AND LOCAL INTENSITY VARIATION PATTERNS

CROSS-REFERENCE TO RELATED APPLICATIONS

This application is a Continuation of U.S. patent application Ser. No. 14/853,682 filed Sep. 14, 2015, which claims priority to, and incorporates herein by reference in its entirety U.S. Provisional Application Ser. No. 62/049,901, filed Sep. 12, 2014, and entitled "SYSTEM AND METHOD FOR AUTOMATIC POLYP DETECTION USING GLOBAL GEOMETRIC CONTRAINTS AND LOCAL INTENSITY VARIATION PATTERNS."

BACKGROUND

The present disclosure relates, generally, to systems and method for processing optical images. More particularly, the disclosure relates to automatic detection of polyps in optical images.

Colonoscopy is the preferred technique for colon cancer screening and prevention, during which a tiny camera is inserted and guided through the colon to detect and remove polyps—precursors to colon cancer. However, a colonoscopy is an operator dependent procedure, wherein human factors, such as fatigue and insufficient attentiveness during colon examination, particularly during back-to-back procedures, can lead to the miss detection of polyps. By some estimates the average polyp miss-rate is between 4 and 12%. Patients with missed polyps may be diagnosed with a late stage cancer with the survival rate of less than 10%.

Computer-aided polyp detection has been a promising approach to reducing polyp miss-rate and encouraging attentiveness during procedures. However, automatic polyp detection remains a challenging task. In particular, shapes of polyps can vary considerably, with the same polyp appearing differently depending on the viewing angle of the colonoscopy camera and spontaneous spasms of the colon. In addition, polyp texture becomes fully visible only if a given polyp appears within the depth of field of the camera. Considering that many cameras have non-adjustable depth of fields, making texture availability dependent on the distance between the polyp and camera. Furthermore, polyp color can vary depending on lighting conditions, appearing in different shades, ranging from dark to saturated colors.

Early works employed color and texture features detected in colonoscopy images to identify polyps. For instance, the work based on color wavelet features sets a representative example. However, the effectiveness of such methods is limited by partial texture visibility of polyps during a colonoscopy procedure, as well as large color variations among polyps. More recent techniques have considered shape, spatio-temporal, and appearance features. Specifically, some groups have attempted use of elliptical-shaped features, while others have employed valley information to localize polyps. However, geometric features in the absence of contextual clues can be misleading, while valley information may result in false detections particularly around wrinkles and vascular structures. Moreover, spatio-temporal features are only suitable for off-line processing of colonoscopy videos, given that such methods require information from the past and future frames for polyp localization at a current frame.

Consequently, considering the limitations of previous technological approaches, it would be desirable to have a system and method for accurate and reliable polyp detection in optical colonoscopy images in real time.

SUMMARY

The present disclosure overcomes the aforementioned drawbacks by providing a system and methods for automated polyp detection in optical colonoscopy images. Specifically, a new methodology is described, which integrates global geometric constraints of polyps with the local patterns of intensity variation across polyp boundaries. The former drives a polyp detector towards objects with curvy boundaries, while the latter minimizes misleading effects of polyp-like structures. As will be described, the present disclosure includes a fast and discriminative patch descriptor for precisely characterizing patterns of intensity variation across boundaries, a new two-stage classification scheme for accurately excluding non-polyp edges from generated edge maps, and a novel voting scheme for robustly localizing polyps from the retained edges of refined edge maps.

In one aspect of the disclosure, a system for polyp detection using optical colonoscopy images is provided. The system includes an input configured to receive a series of optical images, and a processor configured to process the series of optical images with steps comprising of receiving an optical image from the input, constructing an edge map corresponding to the optical image, the edge map comprising a plurality of edge pixel, and generating a refined edge map by applying a classification scheme based on patterns of intensity variation to the plurality of edge pixels in the edge map. The processor may also process the series with steps of identifying polyp candidates using the refined edge map, computing probabilities that identified polyp candidates are polyps, and generating a report, using the computed probabilities, indicating detected polyps. The system also includes an output for displaying the report.

In another aspect of the disclosure, a method for polyp detection using an optical colonoscopy image acquired from a subject is provided. The method includes receiving an optical image acquired from a subject, constructing an edge map corresponding to the optical image, the edge map comprising a plurality of edge pixels, and generating a refined edge map by applying a classification scheme, based on patterns of intensity variation, to the plurality of edge pixels in the edge map. The method also includes identifying polyp candidates using the refined edge map, computing probabilities that identified polyp candidates are polyps, and generating a report, using the computed probabilities, indicating detected polyps.

The foregoing and other aspects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

BRIEF DESCRIPTION OF THE DRAWINGS

FIG. 9A is a graphical illustration of a voting map, generated in accordance with aspects of the present disclosure, applied to an example edge pixel oriented at 135 degrees.

FIG. 9B is a resultant voting map for a synthetic scene when generated votes are accumulated in one voting map.

FIG. 9C is a resultant voting map for the same scene of FIG. 9B when generated votes are accumulated voting maps and multiplied.

DETAILED DESCRIPTION

Figure 4B:
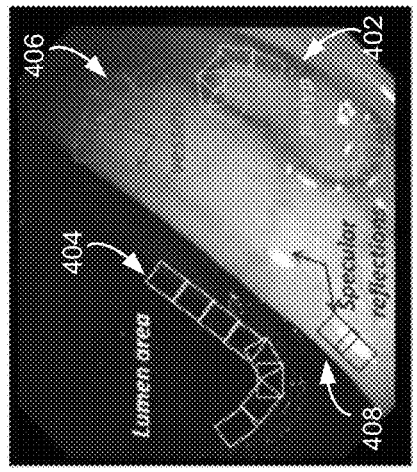
FIG. 4B is a graphical illustration showing how oriented image patches of FIG. 4A are collected from an example optical image.
Figure 4A:
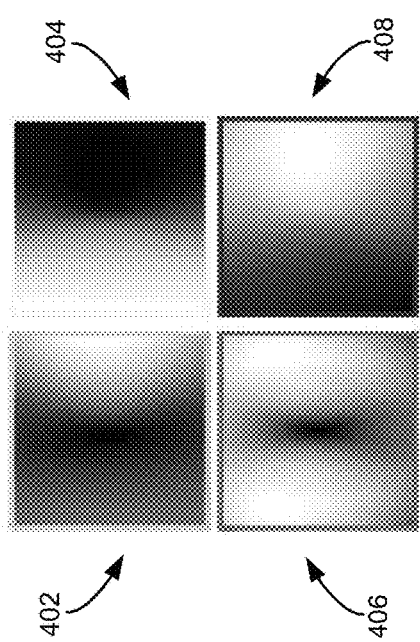
FIG. 4A is a graphical illustration showing the average appearance of polyps, lumen areas, vessels and specular reflection areas obtained using multiple oriented image patches.
Figure 4C:
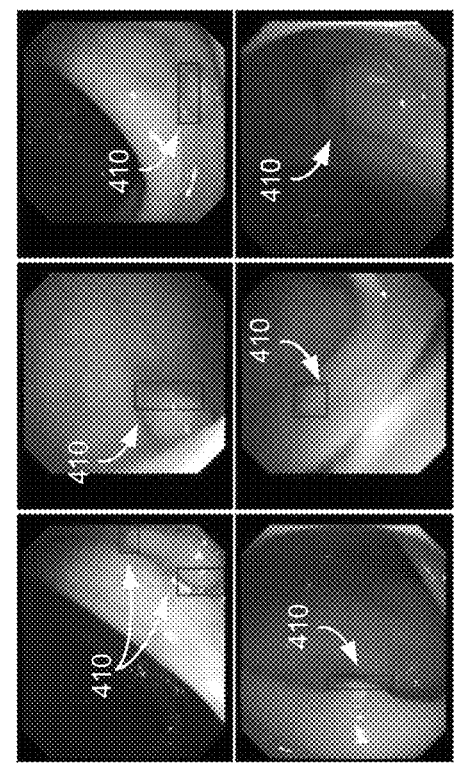
FIG. 4C are optical images of different polyps showing at least one curvy segment at their boundaries.

The present disclosure provides a system and methods for improved polyp detection. In particular, polyps, as compared to other objects present in colonoscopy videos exhibit distinct intensity variations across their boundaries. This is illustrated in FIG. 4a, where the average appearance of hundred thousand oriented image patches around various objects, including polyps 402, lumen areas 404, vessels 406, and specular reflections 408, is compared. Specifically, FIG. 4b shows an example of how oriented patches are extracted from a provided optical image. As appreciated from FIG. 4b, factors that can contribute to the distinct appearance around polyp boundaries include the depth contrast between the polyp side and background side of the boundaries, color contrast between polyps and the colon surface, lighting conditions, and level of polyp protrusion. In addition, polyps, irrespective of their morphology and varying levels of protrusion, feature at least one curvilinear head at their boundaries. This is illustrated in FIG. 4c, where such curvy segments 410 are shown for six different polyps. This is a fundamental characteristic that has been commonly used in polyp detection systems. However, shape features have not been effectively used in detecting polyps due to the complex endoluminal scenes associated with colonoscopy images.

In recognizing the limitations of colonoscopy imaging and variation of polyp appearance, the present disclosure describes a novel detection approach that combines global geometric constraints and intensity variation patterns (IVPs) across identified object boundaries. As will be appreciated from descriptions below, such integration is advantageous over previous methodologies, whereby polyp detection solely based upon object curvature can be easily misled by other structures exhibiting curved geometries.

In some implementations, given a colonoscopy image and its corresponding edge map, patterns of intensity variation across detected boundaries may be captured to remove as many non-polyp edges as possible, followed by a determination as to which side of the retained edges the polyps reside. The former step yields a small subset of candidate edges, thereby minimizing the misleading effects of other polyp-like structures, and the latter allows the retained edges to cast votes regarding the locations of polyps. The votes may then be accumulated in the regions surrounded by high curvature boundaries, to indicate the locations of polyp candidates. Each candidate can then be assigned a probability of being a polyp and those with higher probabilities may be reported, for instance. To integrate the patterns of intensity variation across the boundaries as well as curvature information along the boundaries, the following original contributions are made.

In particular, the present disclosure introduces a new patch descriptor that quickly captures IVPs across boundaries, is rotation invariant and robust against linear illumination changes, and can tolerate small degrees of positional changes, which is important to handle patch misalignment. In addition, a two-stage classification scheme is introduced that enhances low level image features prior to classification by learning a nonlinear similarity metric in the features space. Unlike traditional image classification approaches where a single patch undergoes a processing pipeline, the present approach fuses information extracted from a pair of patches for more accurate classification. Together with the patch descriptor, the present classification scheme filters out non-polyp edges from the determined edge maps. Furthermore, a novel voting scheme is described, which robustly detects objects with curvy boundaries in fragmented edge maps. The voting scheme produces a probabilistic output for each polyp candidate and does not require any predefined parametric model of shapes, nor any information about the size of polyps Evaluations on a public database and other image data demonstrate that the methodology described herein outperforms the state-of-the-art methods.

Figure 1:
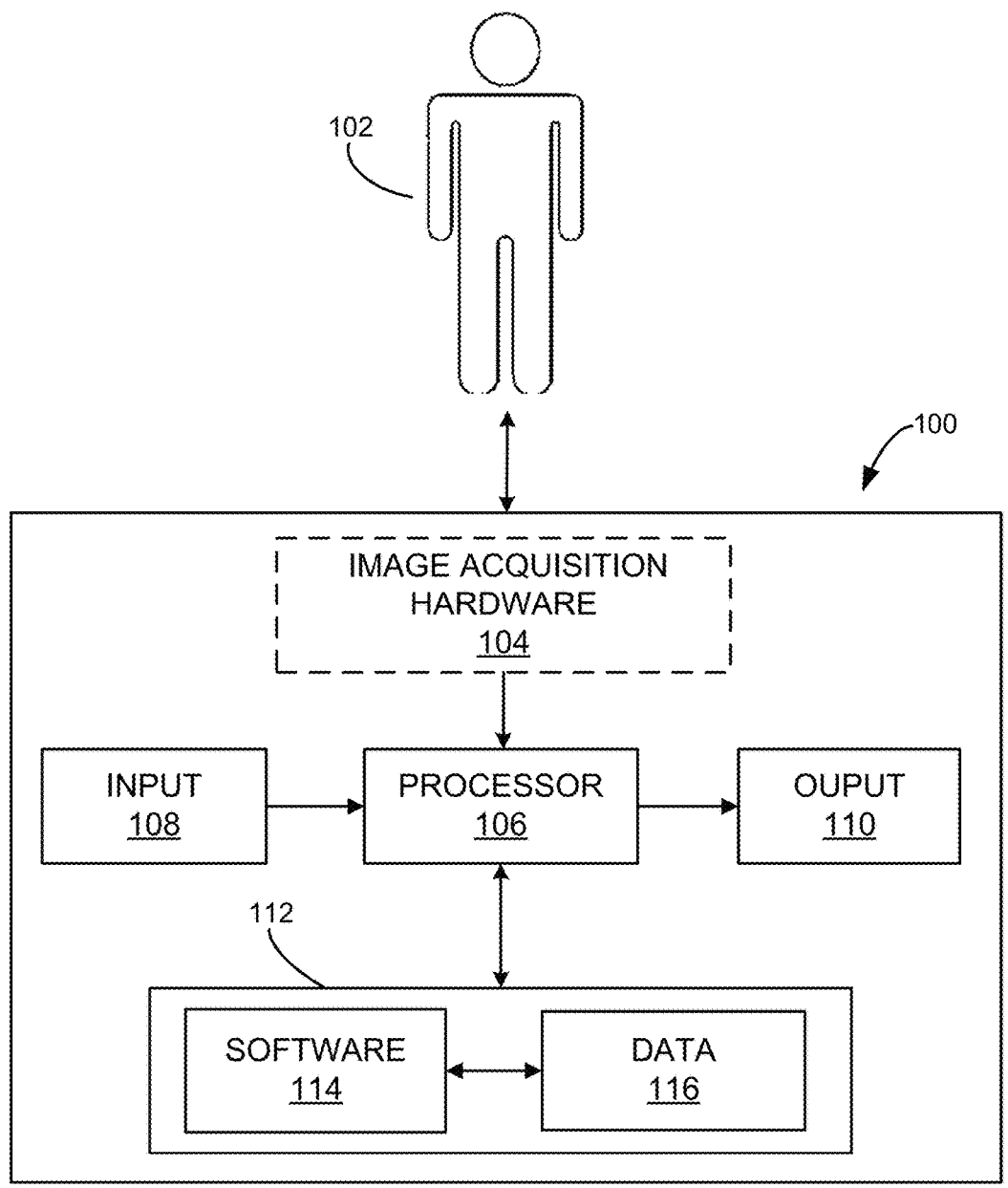
FIG. 1 is a schematic illustration of system for polyp detection using optical images, in accordance with aspects of the present disclosure.

Turning to FIG. 1, a block diagram is shown of an example polyp detection system 100 for detecting polyps in optical images acquired from a subject 102. In general, the polyp detection system 100 may be any device, apparatus or system configured for carrying out instructions for, and may operate as part of, or in collaboration with a computer, system, device, machine, mainframe, or server. In this regard, the polyp detection system 100 may be a system that is designed to integrate a variety of software and hardware capabilities and functionalities. The polyp detection system 100 may operate autonomously or semi-autonomously, or may read executable software instructions from a computer-readable medium (such as a hard drive, a CD-ROM, flash memory and the like), or may receive instructions from a user, or any another source logically connected to computer or device, such as another networked computer or server. The polyp detection system 100 may be, for example, a workstation, a notebook computer, a personal digital assistant (PDA), a multimedia device, a network server, a mainframe or any other general-purpose or application-specific computing device. In some aspects, polyp detection system 100 may be portable, such as a mobile device, tablet, or other portable device or apparatus.

In some configurations, as shown in FIG. 1, the polyp detection system 100 may include image acquisition hardware 104, a processor 106, an input 108, an output 110, a memory 112, and any device for reading computer-readable media (not shown). As such, the polyp detection system 100 may be configured to acquire optical image data using the image acquisition hardware 104 and analyze the data in substantially real-time, while a medical procedure, such as a colonoscopy, is being performed on a subject 102. Alternatively, the polyp detection system 100 may also be configured to access, retrieve and analyze optical image data already stored in memory 112, or other data storage or database.

In some embodiments, the image acquisition hardware 104 may be designed to acquire optical image data continuously or intermittently, for example, during a medical procedure, such as a colonoscopy, and relay the optical image data to the processor 106 for processing. By way of example, the image acquisition hardware 104 can include a camera or other video recording device. In some aspects, the image acquisition hardware 104 may require operator direction, input or feedback, or alternatively may be designed to operate autonomously as directed by the processor 106.

In addition to being configured to carry out steps for operating the polyp detection system 100, the processor 106 may be configured to acquire and/or process optical image data, including image data obtained during a medical procedure, such as a colonoscopy. In one embodiment, the processor 106 may be designed to generate optical images, using optical image data acquired from a subject 102, and apply color filters to the optical images, generating images in several color channels. For example, optical images may be filtered to produce images in the red, green and blue color channels. As will be described, in some aspects, the processor 106 may be configured apply a patch descriptor to capture multiple IVPs across boundaries. In addition, the processor 106 may also be configured to perform a two-stage classification scheme then enhances low level image features prior to classification by learning a nonlinear similarity metric in the features space. Moreover, the processor 106 may further be configured to perform a voting scheme using a refined set of edge pixels, and generate a probabilistic output for each polyp candidate.

The input 108 may take any shape or form, as desired, for operating the polyp detection system 100. In some aspects, the input 108 may be configured to receive a variety of information or selections from a user in the form of different input elements, such as a mouse, keyboard, touchpad, touch screen, buttons, and the like. For instance, the input 108 may be configured for selecting, entering or otherwise specifying parameters consistent with detecting polyps of a requisite or desired size or shape Although not shown in FIG. 1, in some implementations the polyp detection system 100 may also be configured to receive information or data via input 108 directly from an imaging system, storage server, or database, by way of wired or wireless connection, as well as via flash-drive, compact disc, or other computer-readable medium.

The output 110 may take any shape or form, as desired, and may include a visual and/or audio system for providing a report either intermittently or in substantially real time. In some implementations, the report may be in the form of a display for providing a user with visual information associated with a medical procedure, such as a colonoscopy. For instance, raw or processed optical images may be displayed, as well as indicators and locations for objects, such as polyps, vessels, lumens, specular reflections, and so forth, identified using the images. The report may also indicate the probabilities of identified objects being polyps. The report may also be in the form of an audio alert to an operator upon identification of one or more polyps, or other objects. In some aspects, the report may provide instruction to the user for adapting the medical procedure, such as repeating or enhancing imaging of a particular anatomical location.

The memory 112 may contain software 114 and data 116, and may be configured for storage and retrieval of image processing information and data to be processed by the processor 106. In one aspect of the disclosure, the software 114 may contain instructions directed to performing optical image processing for polyp detection, in accordance with aspects of the present disclosure. In another aspect of the disclosure, the data 116 may take the form of optical image data.

Figure 2:
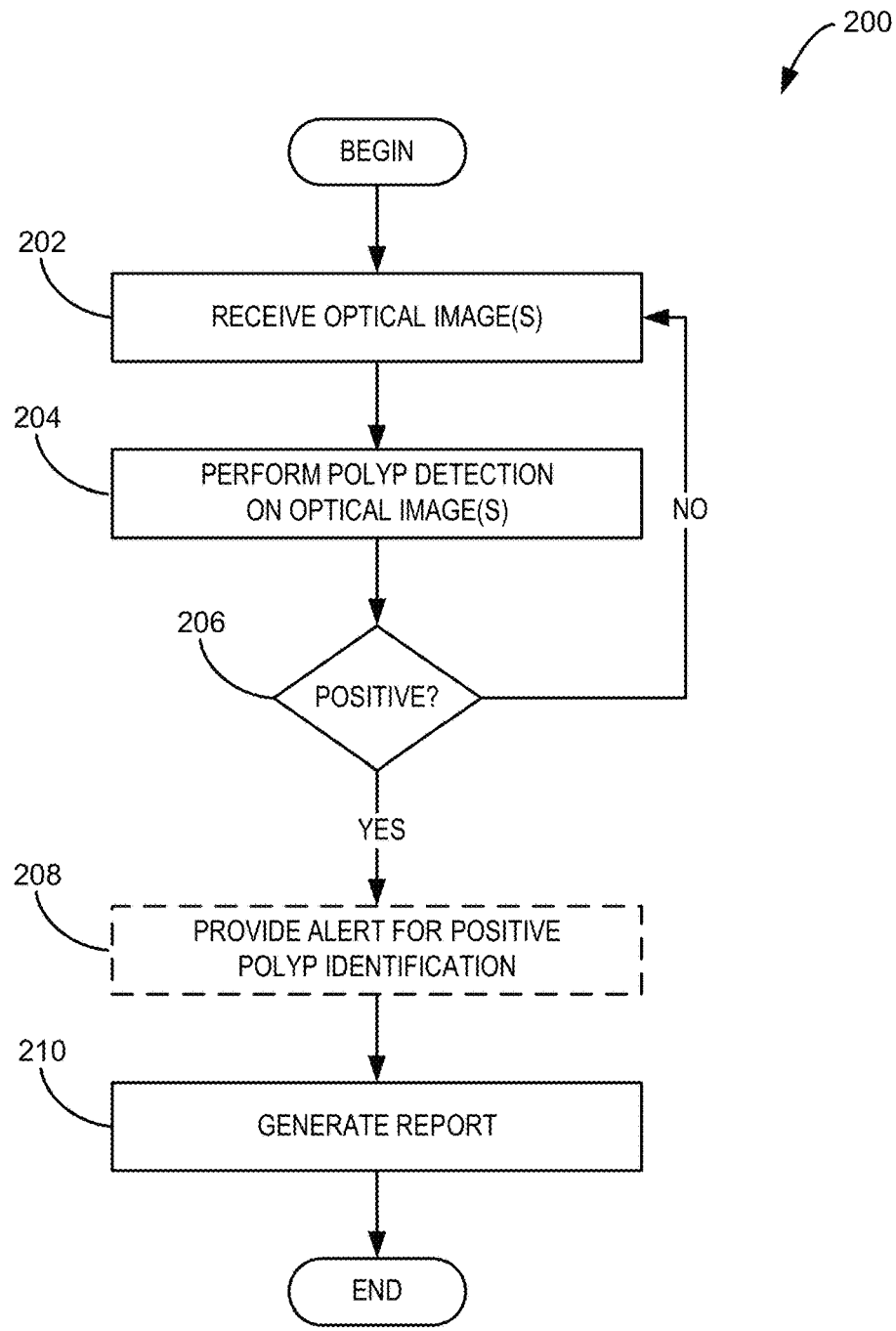
FIG. 2 is a flowchart setting forth steps of a process, in accordance with aspects of the present disclosure.

Turning to FIG. 2, steps of a process 200, in accordance with aspects of the present disclosure, are shown. The process 200 may be carried out using a polyp detection system 100 as described with respect to FIG. 1, or other suitable system. Specifically, the process 200 may begin at process block 202, wherein images or optical image data is received and pre-processed as necessary. In some aspects, optical images or data received at process block 202 may be provided by a live feed, for example, generated using the polyp detection system 100, as described, or other imaging system, or may be retrieved from a data storage location, memory, or database. In addition, information associated with targeted objects, such as colonic polyps, as well as other selections, may also be provided by an operator at process block 202.

At process block 204, a polyp detection step may then be performed using optical images assembled from the provided and/or pre-processed optical image data. In some aspects, optical images may be filtered at process block 204, obtaining multiple color channels for use in generating over-determined edge maps, as will be described. Then, at decision block 206, if polyps, or other objects, are not detected, the above steps may be repeated starting with additional optical images or data being received at process block 202. If polyps, or other objects, are positively identified, then an alert may be provided to an operator to signify such positive identification, as indicated by process block 208. For example, the alert may be in the form of audio signals or visual displays, or instructions to the operator for adapting the medical procedure being performed. Subsequently, at process block 210, a report may be generated, which may take any shape or form. For instance, the report may indicate polyp locations, along with confidence values or probabilities of accurate detection. Steps of the process 200 can be repeated as necessary, or for the duration of the medical procedure performed.

Figure 3:
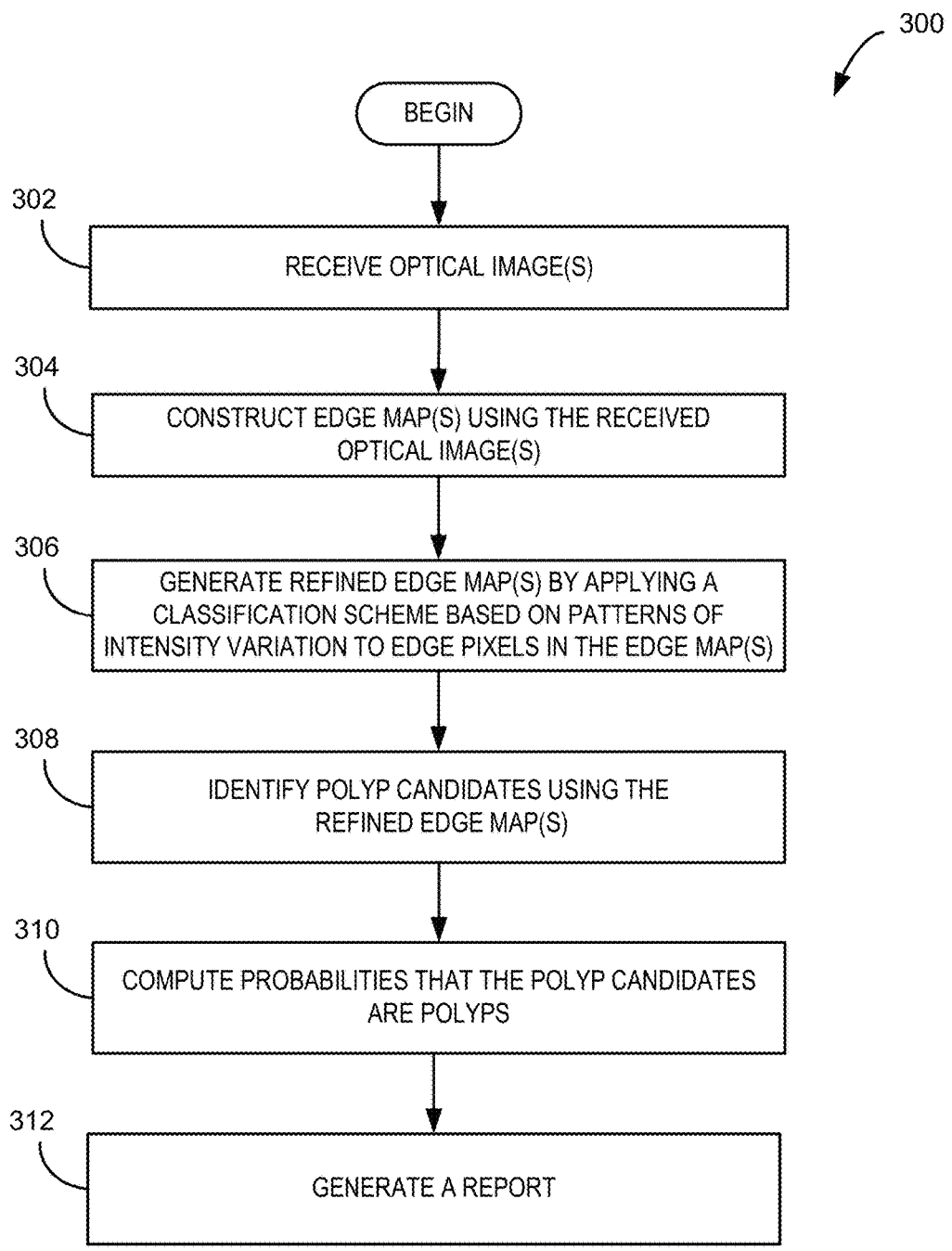
FIG. 3 is another flowchart setting forth steps of a process for polyp detection, in accordance with aspects present disclosure.

Turning to FIG. 3 steps of a process 300 for performing polyp detection, in accordance with aspects of the present disclosure, are shown. In some implementations, process 300 may be carried out using a system described with reference to FIG. 1, or other suitable system. The process 300 can begin at process block 302 with receiving one or more optical images for analysis. As described, such images can be obtained in substantially real time from a live video feed or from a data storage location. The image(s) may then be utilized at process block 304 to construct one or more edge maps, for example, by applying Canny's method of edge detection, for example. In some aspects, one or more color channels associated with the received image(s) may be analyzed to extract as many edges as possible. The constructed edge map(s) may then be processed by applying a classification scheme based on patterns of intensity variation, as will be described, and indicated by process block 306. In this manner, one or more refined edge maps may be generated. The refined edge map(s) may then be used at process block 308 to identify polyp candidates. Probabilities that identified polyp candidates are indeed polyps may then be computed at process block 310. A report may then be generated at process block 312, as described.

Figure 5:
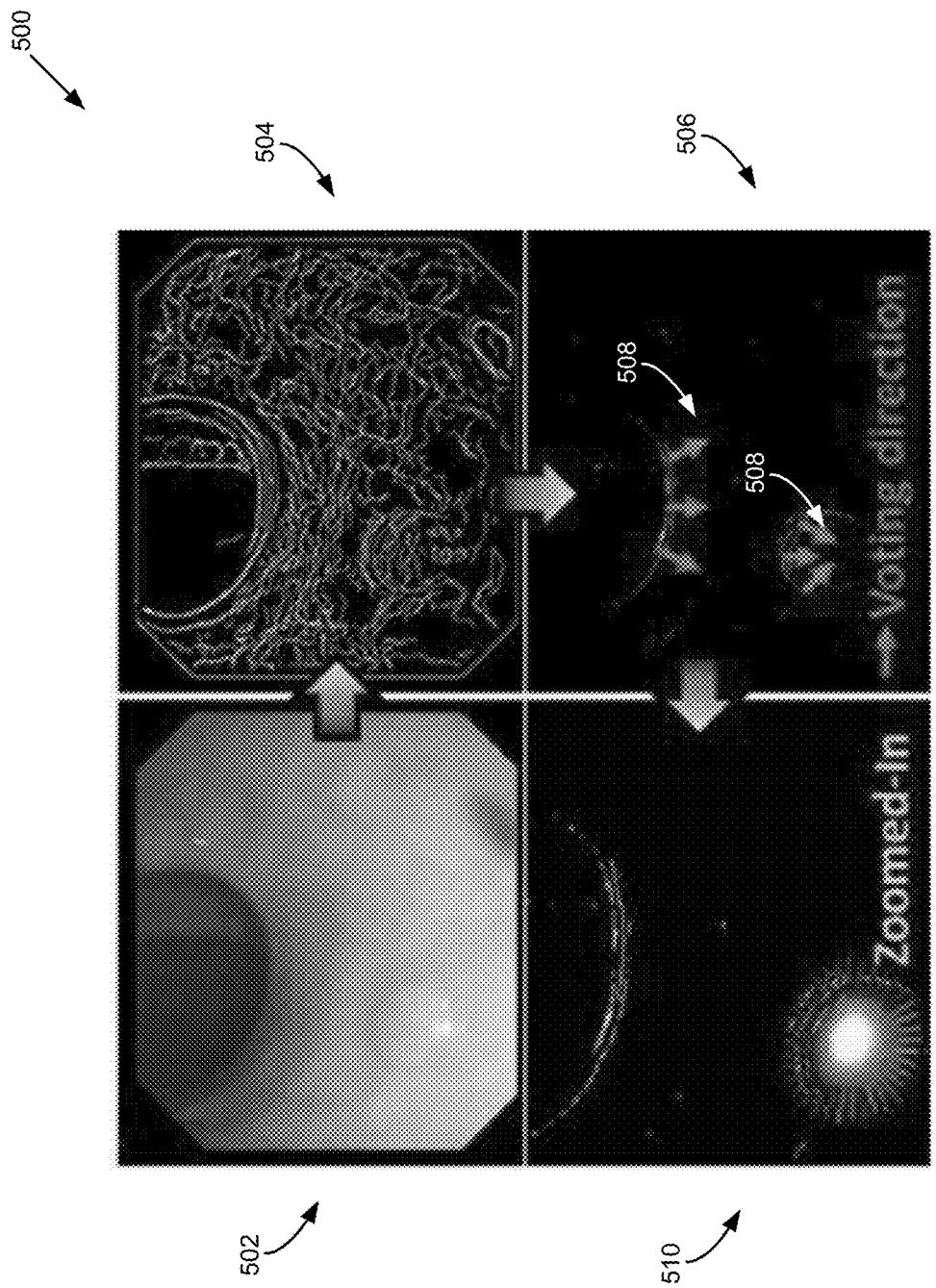
FIG. 5 is a diagram setting forth steps of method for polyp detection, in accordance with the present disclosure.

The above process is visually represented in FIG. 5, whereby given an optical image 502, an edge map 504 comprising a crude set of edge pixels is constructed. The edge map 504 may then be refined to produce a refined edge map 506, effectively removing many non-polyp boundary edges through application of a classification scheme based on IVPs, as described below. At this stage, voting directions 508 may also be inferred by the classifier for each of the retained edges in the refined edge map 506. Shape and curvature information of the retained edges modulated by the inferred voting directions is captured by a voting scheme, as described below. As shown in the heat map 510, the votes are accumulated in the regions surrounded by high curvature. The pixel with maximum vote accumulation may be considered as the polyp candidate. A band, or set of line segments in its discrete form, may be then placed around the identified candidate to measure the probability of being a polyp candidate. The fraction of the line segments that hit the retained edges and meet pre-selected requirements determined the polyp likelihood for the generated candidate. The above steps are further detailed below.

Edge Map Construction

To generate edge maps, formed by a number of edge pixels, any suitable algorithm may be used. For example, a Canny edge detection may be applied to one or more separate color channels, such as a red, green and blue color channels, of a provided optical image. In this manner, an over-complete edge map may be generated. Once edge maps are constructed, edge directions for all pixels in the maps may also be estimated. Edge directions can be used to extract oriented patches around the edge pixels, as will be described. In particular, Canny's algorithm computes edge directions based on the local image gradients in horizontal and vertical directions. Alternatively, edge directions may also be determined using a ball tensor voting technique. Other techniques are also possible. Specifically, in ball tensor voting, the edge direction of an edge pixel is determined according to the arrangements of the surrounding edge pixels such that the continuation of the edge directions is maintained. In fact, the locations of nearby edges determine the edge direction of a central pixel. It is therefore, unlikely to obtain an inconsistent or non-smooth orientation map. This is in contrast to other traditional edge detection techniques that discard the configuration of the surrounding edge pixels.

Feature Extraction

The goal of feature extraction is to capture IVPs in an image patch around each edge pixel, and includes three major requirements: (1) the ability to be fast to handle a large volume of input patches from the edge detection stage; (2) the ability to provide high level of illumination invariance, since in a colonoscopy procedure, the source of light moves along with the camera, causing the same segment of a boundary to appear with varying contrast in a number of consecutive frames; (3) the ability to provide rotation invariance against the edge orientations because the essential information do not lie along edge directions but across the edges.

A patch descriptor, in accordance with aspects of the present disclosure, may begin by extracting a patch along the orientation of any given edge pixel such that the edge segment appears vertically in the middle of the patch. This presentation provides two advantages: (1) image appearance characterization independent of edge orientations, and (2) some degrees of robustness against positional variability along the horizontal axis. Then sub-patches of a size say n×m may be formed all over an extracted patch, for example, with 50% overlap along horizontal and vertical directions. Each patch may then be averaged vertically, resulting in a 1D intensity signal $S_i$, decreasing positional variability along the vertical direction. To obtain a compact and robust presentation of intensity variations, a 1D discrete cosine transform (DCT) may be applied to the extracted signal:

$$C_k = \frac{2}{n} w(k) \sum_{i=0}^{n-1} S_i \cos\left(\frac{2i+1}{2n}\pi k\right) \quad (1)$$

where $w(k)=1/\sqrt{2}$, $k=0$ and $w(k)=1, 1 \leq k \leq n-1$. DCT has a strong energy compaction property, allowing the entire spatial information to be summarized in a few coefficients. However, such a compact presentation of the signal is not robust against illumination changes. A constant change in the intensity of the pixels in a patch directly appears in the DC coefficient, and illumination scaling affects both the DC and AC coefficients. To achieve invariance against constant illumination changes, the DC component may be discarded, while to achieve invariance against linear intensity changes, the AC components may be normalized using their $L^2$-norm. However, this scheme is not efficient given interest in only a few of the AC components. Therefore, the first few AC coefficients may be computed from each patch and their $L^2$-norm used for normalization, achieving a significant performance speedup. Finally, the coefficients selected from each sub-patch may be concatenated to form a feature vector for the extracted patch.

The above-described patch descriptor has several distinct advantages. First, it is very fast because it avoids 2D DCT by compressing each sub-patch into a 1D signal, requiring the computation of only a few DCT coefficients from each sub-patch. Second, due to the normalization treatment applied to the DCT coefficients, the patch descriptor achieves invariance to linear illumination changes and partial tolerance against nonlinear illumination variations over the entire patch, particularly if the nonlinear change can be decomposed to a set of linear illumination changes on the local sub-patches. Third, the patch descriptor provides a rotation invariant presentation of the intensity variation patterns due to the consistent appearance of the edge segments in the oriented patches. Fourth, the patch descriptor handles small positional changes, which is essential for coping with patch variations caused by edge mis-localization. In practice, spurious edges around polyp boundaries and Gaussian smoothing prior to applying a Canny edge detector can cause inaccurate edge localization, where an edge pixel can found a few pixels away from the actual location of the boundary. As such, it is important for a patch descriptor to provide a consistent image presentation in the presence of such positional changes. Positional variability can be decreased by selecting and averaging overlapping sub-patches in both horizontal and vertical directions.

In some aspects, DCT may more suitable for the provided patch descriptor than the other transforms such as Discrete Sine Transform (DCT), Discrete Fourier Transform (DFT), and Discrete Wavelet Transform (DWT). Compared to DFT and DST, DCT enables energy compaction for a wider range of intensity signals and thus provides a more efficient and informative image presentation. More specifically, DFT assumes that the intensity signal S is a part of a periodic signal; therefore, if the intensity values at both ends of the intensity signal are not equal ($S[0] \neq S[n-1]$), S will appear as a part of non-continuous periodic function to DFT. As such, one can expect large high-frequency Fourier coefficients, which prevents the information (energy) of the signal to be compressed in a few Fourier coefficients. Large high frequency components can also appear in the case of DST, if the intensity signals have non-zero values at their both ends ($S[0] \neq 0$; $S[n-1] \neq 0$). This constraints requires the corresponding sub-patches to appear dark in the left and right borders, a constraint that is not often met in practice. In contrast, DCT relaxes these constraints, requiring only smooth behavior at both ends of the intensity signals. This is a more practical assumption given that intensity profiles do not change abruptly except at strong edges and that the intensity signals are computed by vertically averaging the corresponding sub-patches, which further smoothes the intensity signals. As such, DCT may be preferable over DWT because it allows for intuitive feature selection and incurs less computational burden. Also, DCT requires only one parameter: the number of selected coefficients from each subpatch, which can be determined both experimentally and intuitively.

Figure 6:
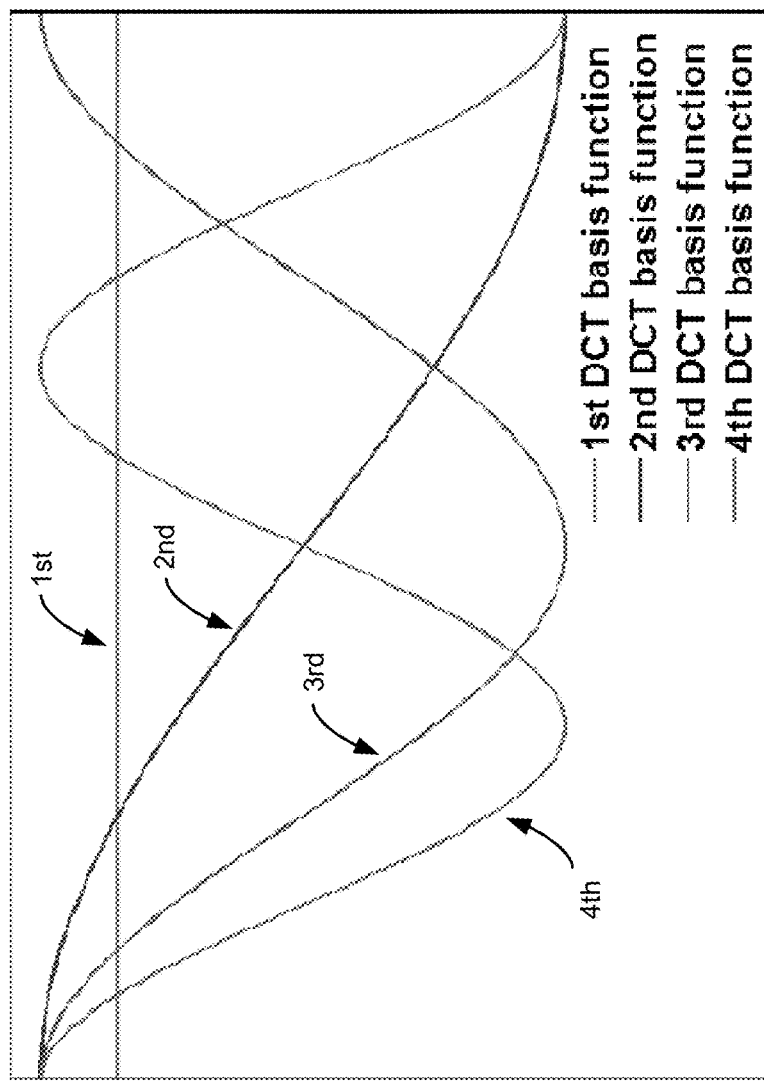
FIG. 6 is a graph showing the first 4 discrete cosine transform (DCT) basis functions used for feature computation, in accordance with aspects of the present disclosure.

By way of example, FIG. 6 shows the first 4 DCT basis functions that may be used for feature computation. As seen, the first basis function corresponds to the DC component, the second one measures whether the intensity in signal S is monotonically decreasing (increasing) or not, the third one measures the similarity of the intensity signal against a valley (ridge), and finally the fourth one checks for the existence of both a valley and a ridge in the signal. The higher order basis functions are suitable for detecting high frequency variations in the intensity signal; however, such high frequency content may not be reliable as they are susceptible to noise and degradation factors in the images. Therefore, one can intuitively set the number of desired coefficients without resorting to more complicated feature selection algorithms. In contrast, DWT requires the tuning of more parameters such as the choice of wavelet function or the number of decomposition levels, resulting in a large number of wavelet coefficients, which demands an appropriate feature selection mechanism to produce an efficient image presentation.

Edge Classification

A classification scheme, in accordance with aspects of the present invention, aims to (1) remove as many non-polyp edges as possible and (2) determine on which side of the retained edges a polyp exists—hereafter, referred to as the voting direction, (see FIG. 5). To achieve the two objectives, a two-stage classification scheme is provided, which analyses a pair of oriented patches around a given target edge pixel, and then depending on the appearance of image pair classifies the edge as either polyp or non-polyp. In the case of a polyp edge, the classification scheme identifies on which side of the boundary the polyp is present. In particular, the first stage determines a nonlinear metric in the low level feature space to measure the similarities between the input patches and some predefined structures. Such structures may be chosen through a misclassification analysis. The second stage performs the main classification, removing non-polyp edges and determining voting directions for the retained edges. In the following, the collection of image pairs is explained, followed by description of the classification scheme.

Figure 7:
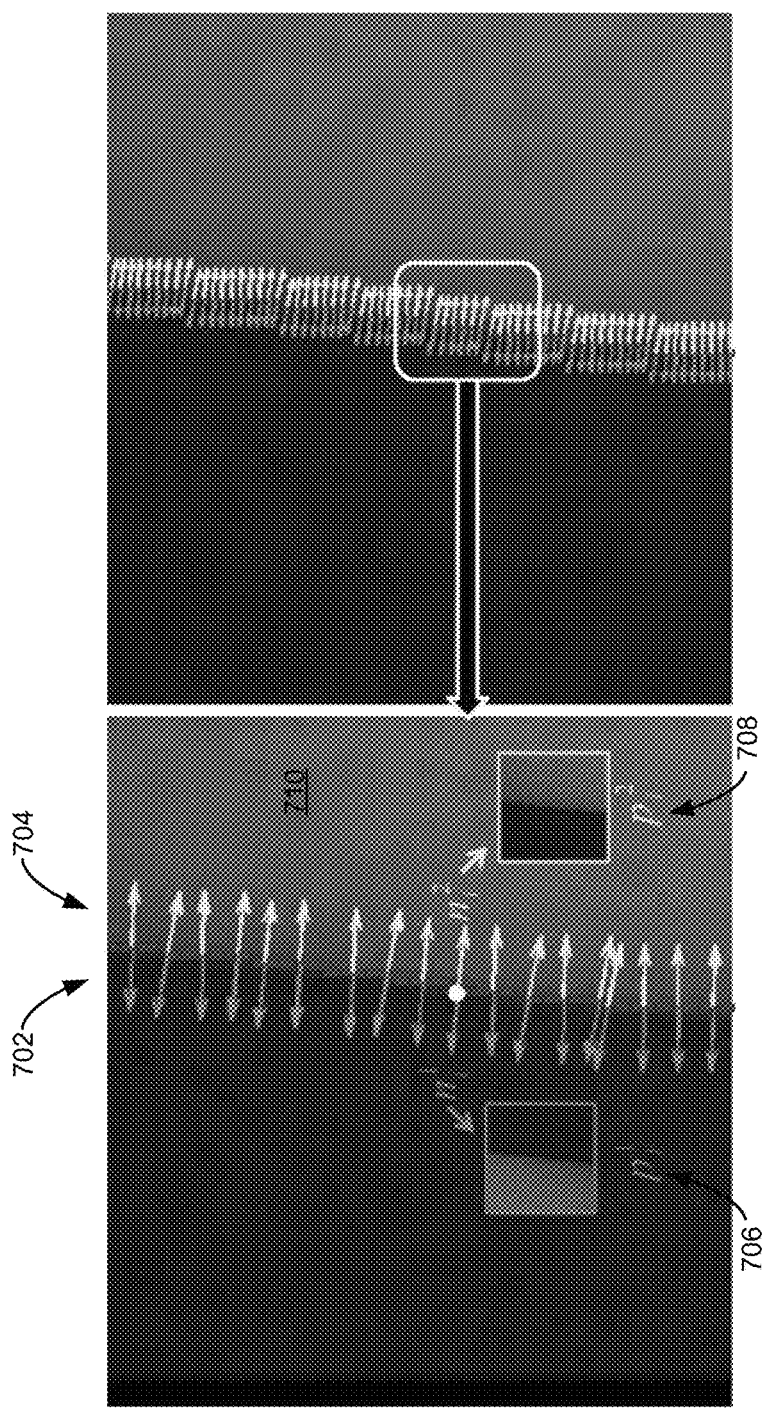
FIG. 7 is a graphical illustration showing how patches are extracted from an object boundary, in accordance with aspects of the present disclosure.

For an edge pixel at angle θ on the boundary of a polyp, one can obtain two normal directions by applying 90 degree clockwise and counterclockwise rotations on the edge direction vector. This is illustrated in FIG. 7, where pairs of normal directions $\{n_i^1, n_i^2\}$ for a set of edge pixels on a polyp boundary are depicted using arrows 702 and 704 respectively. To extract an oriented image around an edge pixel, the image is interpolated along the normal and edge directions. However, given the two normal directions one can obtain a pair of patches $\{p_i^1, p_i^2\}$ around each edge pixel, as indicated by arrows 706 and 708, respectively. The present classification scheme operates on each image pair and then combines their information not just to classify the underlying edge into polyp and non-polyp categories, but to determine the desired normal direction among $n_i^1$ and $n_i^2$ that points towards the polyp location. Such desired normal direction is referred herein as the "voting direction." Referring again to FIG. 7, assuming that the gray area 710 corresponds to a polyp region, all the green normal vectors show the voting directions because they all point to the polyp location, as indicated by arrows 704.

As described, present classification scheme has 2 stages. In the first stage, the image appearance may be learned around the boundaries of the structures of interest in contrast to random structures in colonoscopy images. The structures of interest are chosen through a misclassification analysis and may consist of polyps, vessels, lumen areas, and specular reflections. A 5-class classifier can be trained based on the features generated by a patch descriptor, as described, to distinguish between such boundaries in the images. In other words, the classifier learned in the first stage measures the similarities between the input patches and the predefined structures by learning a non-linear metric in the low level feature space. The first layer can be also viewed as a feature enhancer that takes low-level image features from the proposed patch descriptor and produces mid-level semantic features.

The key to training the above classifier is to have a set of aligned patches where the structure of interest consistently appears on one side (e.g., left) and the background on the other side (e.g., right) in all the collected patches. To that end, the normal directions prior to image interpolation can be chosen such that they all point towards or away from the structures of interest. Doing otherwise would result in the arbitrary appearance of the structure of interest on left or right side of the collected patches. This is may be appreciated from FIG. 7 where depending on the choice of the normal direction the polyp (the gray region 710) appears on the left or right side of the patches.

To achieve patch consistency, a ground truth for the structures of interest may be utilized. The ground truth definition depends on the structure of interest. For instance, for polyps, the ground truth may be a binary image where the polyp region is white and background is black. When extracting polyp patches, the normal direction may then be chosen such that it points towards the white region. For lumen areas and specular spots, the ground truth may still a binary image but the white region can corresponds to the dark lumen and the bright specular reflection, respectively. For vessels, the binary ground truth could show only the locations of vessels. A preferred normal directions is not required because the image appearance around the vessels is most often symmetric. For random structures, image patches may be collected at random edge locations in colonoscopy images with arbitrary choice of normal directions.

Figure 8:
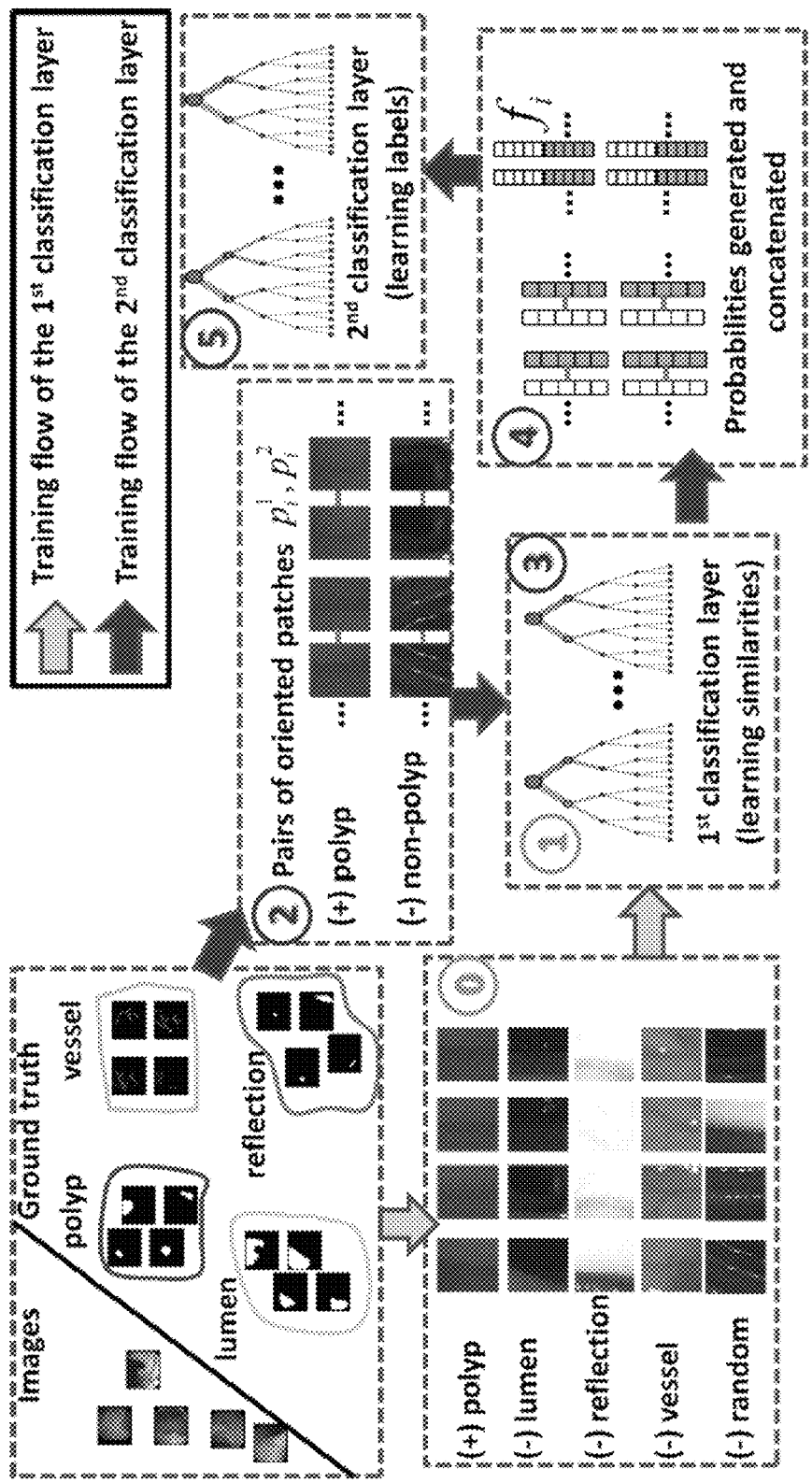
FIG. 8 is a diagram showing the training stage of a classification scheme, in accordance with aspects of the present disclosure.

The goal of the second classifier is to group the underlying edges into polyp and non-polyp categories and determine the desired normal directions. As such, the second classifier may be trained based on the pair of patches in the mid-level feature space, which is generated by the first classifier. A pair of patches may be sued because for a new image no information about the polyp location nor about the desired normal directions may be available. Therefore, a pair of patches may be extracted around each edge pixel, applying the classifier trained in the first stage to produce similarity features, and then performing edge classification using the second classifier by combining the similarity feature computed for the image pair. The training process of the suggested classification scheme is illustrated in FIG. 8 and is further explained in the following step-wise guide.

Step 0: The space of negative patches is divided into 4 sub-classes: vessels, lumen areas, specular reflections, and a class containing other structures in the scenes. These four categories together with the polyp class constitute the structures of interest. Given the ground truth in a given database of optical images, a stratified set of $N_1=100,000$ oriented patches around these five types of boundaries may be collected in a manner such that the structures of interest always appear on the same side of the patches. This is to ensure a consistent presentation for all structures.

Step 1: A 5-class classifier may then be trained to learn the appearance of these 5 types of structures in the low level feature space that is generated by a patch descriptor in accordance with the present disclosure. The trained classifier can be viewed as a similarity learner module and its five probabilities for each input patch can be viewed as mid-level image features in contrast with the low level input features, which mainly encode IVPs across boundaries.

Step 2: A stratified set of $N_2=100,000$ pairs of oriented patches may be collected from polyp and non-polyp boundaries in training optical images provided. Let $\{p_i^1, p_i^2\}$ be the extracted pair of patches around the ith edge with the corresponding normals, $\{n_i^1, n_i^2\}$, where $\angle n_i^1 \in [0,\pi]$ and $\angle n_i^2 = n_i^1 + \pi$. Note that the normal vector indicates the interpolation direction when extracting oriented patches. Based on the state of the $i^{th}$ edge, a label $y^i$ is assigned to this pair of patches, where "0" represents a non-polyp edge, "1" represents a polyp edge with $n_i^1$ indicating the voting direction, and "2" is for a polyp edge with $n_i^2$ indicating the voting direction, $\{(p_i^1, p_i^2, y^i) | y^i \in \{0,1,2\}, i=1,2,\ldots,N_2\}$.

Step 3 and 4: low level features are extracted from each pair of patches and then the classifier trained in the first layer is applied, resulting in two arrays of mid-level features per pair that are further concatenated to form a feature vector, $\{(f^i, y^i) | y^i \in \{0,1,2\}, i=1,2,\ldots,N_2\}$.

Step 5: Once all feature vectors are collected, a 3-class classifier is trained to learn both edge labels and voting directions. For both layers, a random forest classifier may be chosen, given its high quality probabilistic output.

Given an edge map for a test image, a pair of patches is extracted for every edge pixel and then the corresponding low level features are computed. Next, each feature vector is fed to the first classification layer. The mid level features generated from each pair of patches are concatenated and fed to the second classification layer where an edge pixel may be declared as a polyp edge if the corresponding probability dominates that of the other two classes: $p(y_i, c) > p(y_i \neq c)$, $c \in \{1,2\}$ which may be met if $p(y_i = c) > 0.5$, $c \in \{1,2\}$. Therefore, an underlying edge of each pair of patches may be classified according to the rule:

$$\begin{cases} \text{"polyp" and } n_i^* \leftarrow n_i^1 & \text{if } p(y^i = 1) > 0.5 \\ \text{"polyp" and } n_i^* \leftarrow n_i^2 & \text{if } p(y^i = 2) > 0.5 \\ \text{"non-polyp"} & \text{otherwise.} \end{cases} \quad (2)$$

where $n_i^*$ is the desired normal direction or voting direction. The other alternative to Eqn. 2 is to assigned the edge pixel to the class with maximum probability. Once all the edge are classified, non-polyp edges are removed from the edge map and the remaining edges, along with their corresponding voting directions, are provided to the vote accumulation scheme for polyp localization, as described below.

To demonstrate the advantage of the second classification stage, consider edge classification scenario where only the first classifier is used for groping the edge pixels. After a pair of patches pass the first classifier, two sets of probabilities are obtained. To determine a polyp edge, one can compare the polyp probabilities between the two patches and see if the larger probability dominates. The desired normal direction is also determined according to the normal direction of the patch with larger probability. However, a problem arises when there exists more than one dominating class. For instance, consider the following two sets of probabilities computed for a pair of patches, {0.7, 0.1, 0.0, 0.0, 0.2} and {0.0, 0.3, 0.1, 0.6, 0.0} which suggests two dominating classes. This corresponds to patch $p_i^1$ around $i^{th}$ edge resembling the appearance of a polyp boundary, while the counterpart patch $p_i^2$ resembling the boundary appearance of specular reflections. To come to a decision regarding the underlying edge pixel, one can rely on the first patch and declare a polyp edge with edge normal being $n_i^1$, or consider information from the counterpart patch and declare a non-polyp edge. One way to resolve the issue is to declare a polyp edge if there exists only one dominating class; however, this may result in a large number of false negative edges. To eliminate the need for sub-optimal user defined rules, a second classifier can then be in the mid-level feature space to learn such relationships and utilize them for more accurate edge classification.

Voting Scheme

Edges that have passed the classification stage, as described above, are referred herein as the "voters." Each voter has a polyp direction ni and a classification confidence $C_{v_i} = \max(p(y^i=1), p(y^i=2))$. A voting scheme, in accordance with the present disclosure, may begin with grouping the voters into K categories according to their voting directions, $$V^k = \left\{ v_i \ \bigg| \ \frac{k\pi}{K} < \angle n_i^* < \frac{(k+1)\pi}{K} \right\}, k = 0, \ldots K.$$

Such edge grouping prior to vote casting minimizes vote accumulation in the regions that are surrounded by low curvature boundaries. The voters in each category then cast votes at their surrounding pixels according to their voting directions and classifications confidence. This results in K voting maps that are further multiplied to form the final voting map whose maximum vote accumulation (MVA) indicates the location of a polyp candidate. Mathematically, $$MVA = \operatorname*{argmax}_{x,y} \prod_{k=1}^{K} \sum_{v \in V_k} M_v(x, y), \quad (3)$$

where $M_v(x, y)$ is the vote cast by the voter v at a receiver pixel r=[x, y], which is computed as follows:

$$M_v(x, y) = \begin{cases} C_v \exp\left(\frac{-\|\vec{v}\|^2}{\sigma}\right) \cos(\angle \vec{n}^* \vec{vr}), & \text{if } \angle \vec{n}^* \vec{vr} < \pi/2 \\ 0, & \text{if } \angle \vec{n}^* \vec{vr} \geq \pi/2 \end{cases} \quad (4)$$

where σ controls the size of the voting field. FIG. 9A shows an example voting field for an edge pixel lying at 135 degree. As seen, the votes are cast only in the region pointed by the voting direction. Such selectivity arises from the condition set on $\vec{n}^*\vec{vr}$, which prevents the voters from casting votes in the opposite direction. The exponential and cosinusoidal decay functions enable smooth vote propagation, which are used to determine the likelihood of a polyp candidate.

In some aspects, it may be advantageous for the above-described voting scheme to prevent vote accumulation in the regions that are surrounded by low curvature boundaries. As described, polyps appear as objects with curvy boundaries; therefore, such regions, in general, cannot represent polyps. Grouping edges prior to vote casting and multiplying the resultant voting maps may thus fulfill this requirement. This is because the boundary pixels that surround such regions contribute to only a small fraction of the K to-be-multiplied voting maps and thus after multiplication vote accumulation within these regions reduces to a minimum. To illustrate this, a synthetic image may be generated whose edge pixels are arranged on a polyp-like structure and a set of parallel lines. FIG. 9B shows the voting map when all the voters independent of their voting direction contribute to only one voting map. As seen, the votes are accumulated in two regions: inside the curvy structure which is desirable, and between the parallel lines which is undesirable. FIG. 9C shows the voting map for the same image when edge grouping and map multiplication are employed. As seen, the accumulator assigns low values to the region between the parallel lines, and high values to the region inside the polyp-like structure.

Figures 10A, 10B:
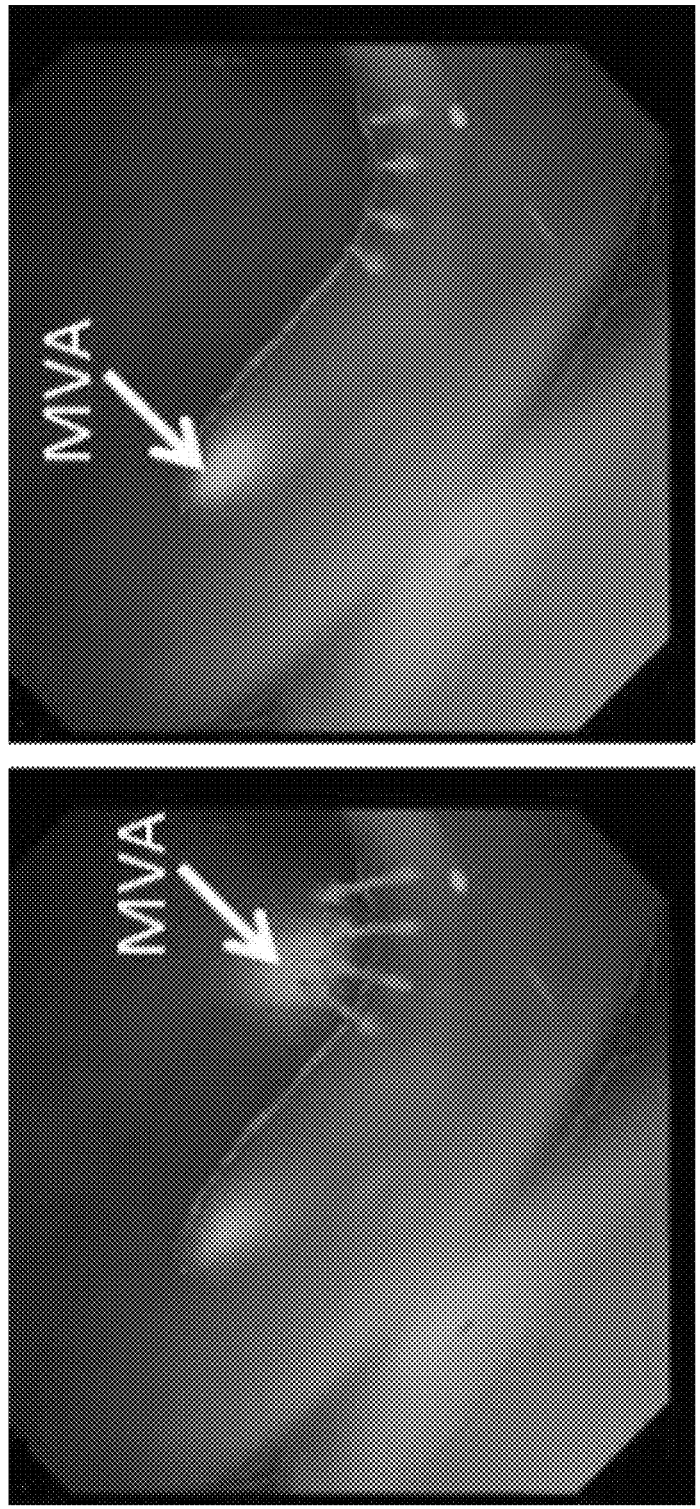
FIG. 10A is an example colonoscopy image where voters cast votes along both possible normal directions, leading to inaccurate polyp identification.
FIG. 10B is the same example colonoscopy image of FIG. 10A with voters cast votes only along the voting directions, leading to accurate polyp identification.

Another important characteristic of the present voting scheme is the utilization of voting directions that, as shown in FIG. 9A, limits a voter to cast votes only along its assigned voting direction. Ignoring voting directions and allowing voters to vote along both possible normal directions result in vote accumulation on both sides of the boundaries, which often leads to polyp mislocalization. This is illustrated in the example of FIG. 10A, where no selectivity in voting directions causes polyp mislocalization. However, by contrast, including such a selectivity allows for correct polyp localization, as shown in FIG. 10B.

Probability Assignment

Figure 11:
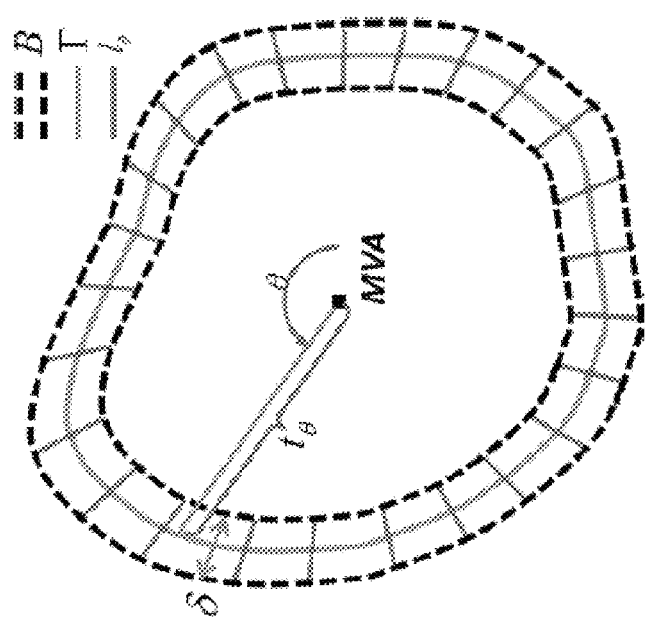
FIG. 11 is a graphical illustration of narrow band determination for assigning probability score to a polyp candidate, in accordance with the present disclosure.

The maximum vote accumulation at a polyp candidate may depend on many factors including the size of polyps and the number of nearby voters around polyps. Therefore, it may not be suitable to use raw accumulated votes to assign a probabilistic score to a polyp candidate. Alternatively, a search for the contributing voters may be done within a narrow band around the polyp candidate. A narrow band B, as shown in the example of FIG. 11, consists of radial line segments whose extension passes through the candidate location. A line segment $l_\theta$ can be parametrized as MVA+t $(\cos(\theta),\sin(\theta))^T$ with $t \in [t_\theta-\delta/2, t_\theta+\delta/2]$ where δ is the bandwidth, and $t_\theta = \|\Gamma_\theta - MVA\|$ is the distance between the candidate location and the corresponding point on the band skeleton Γ. To form the band around a polyp candidate, one needs to determine the bandwidth δ and a set of distances $t_\theta$. These parameters may be estimated from the corresponding voting maps. Once the band is formed, the probability assigned to a polyp candidate can be calculated as $$\frac{2}{|S_\theta|} \sum_{\theta \in S_\theta} (I_\theta \vee I_{\theta+180}),$$

where $S_\theta$ denotes the set of angles along which the voters are searched for and $|S_\theta|$ is the cardinality of $S_\theta$. The discrete set $S_\theta = \{\theta | 0 \leq \theta \leq 180\}$ may be considered for probability computation. In this equation, $I_\theta$ is an indicator variable that takes the value 1 if the line segment $l_\theta$ hits at least a voter v whose estimated polyp direction $n^*_v$ points toward the candidate location. This equation is designed to be sensitive to both regions surrounded by continuous boundaries and those surrounded by partially segmented and discontinuous boundaries.

Narrow Band Determination

Isocontours of a voting map may be defined for use in estimating the unknown parameters of the bands. The isocontour $\Phi_C$ of the voting map V is defined as $\Phi_C=\{(x,y)|V(x,y)=cM\}$, where M denotes the maximum of the voting map and c is a constant between 0 and 1. In some aspects, shapes of isocontours may be used to infer the shape of the band such that it contains a polyp boundary. As will be shown, isocontours of a voting map can predict where an actual object boundary is located.

Figure 12B:
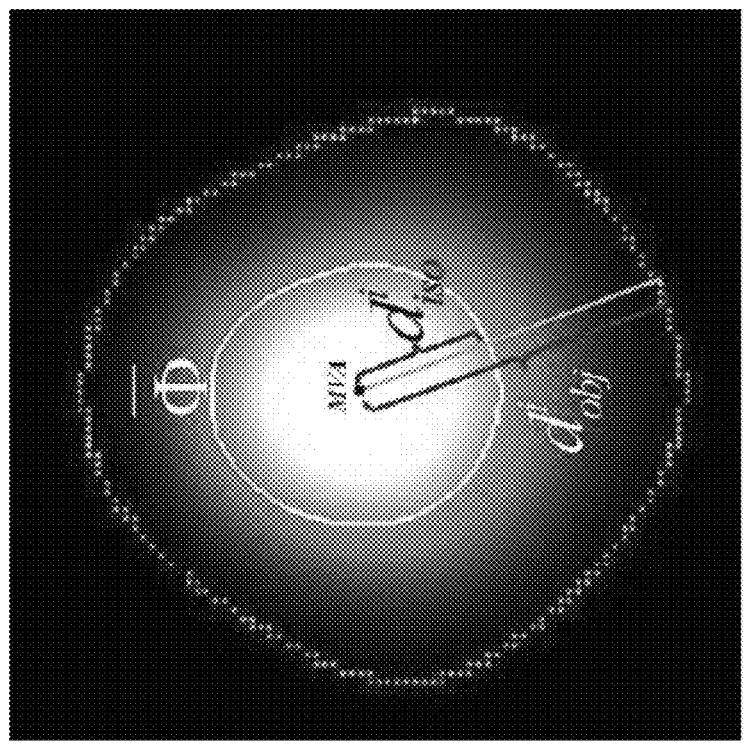
FIG. 12B is a graphical illustration showing a representative isocontour of a voting map, generated using isocontours as shown in FIG. 12A.
Figure 12A:
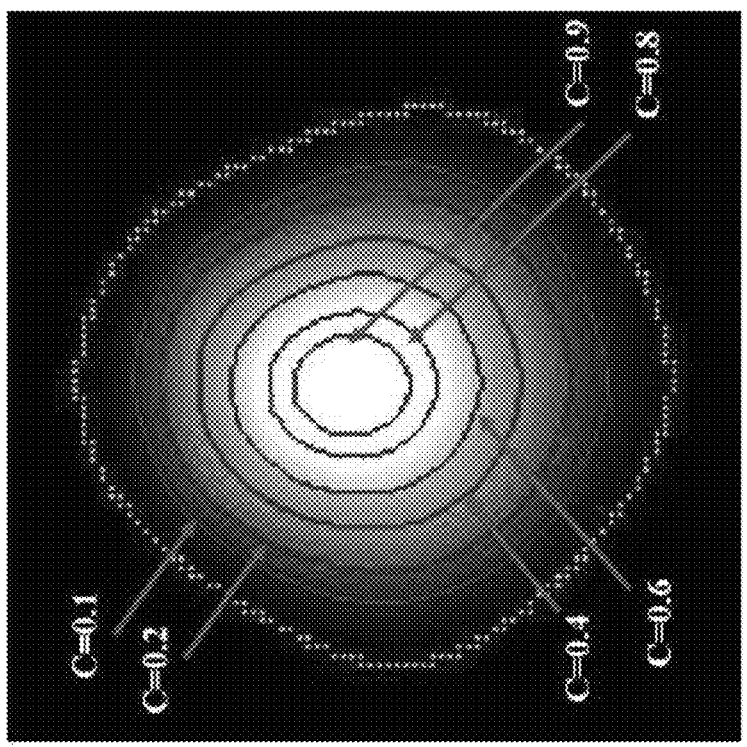
FIG. 12A is a graphical illustration showing isocontours for a synthetic shaped object.
Figure 13:
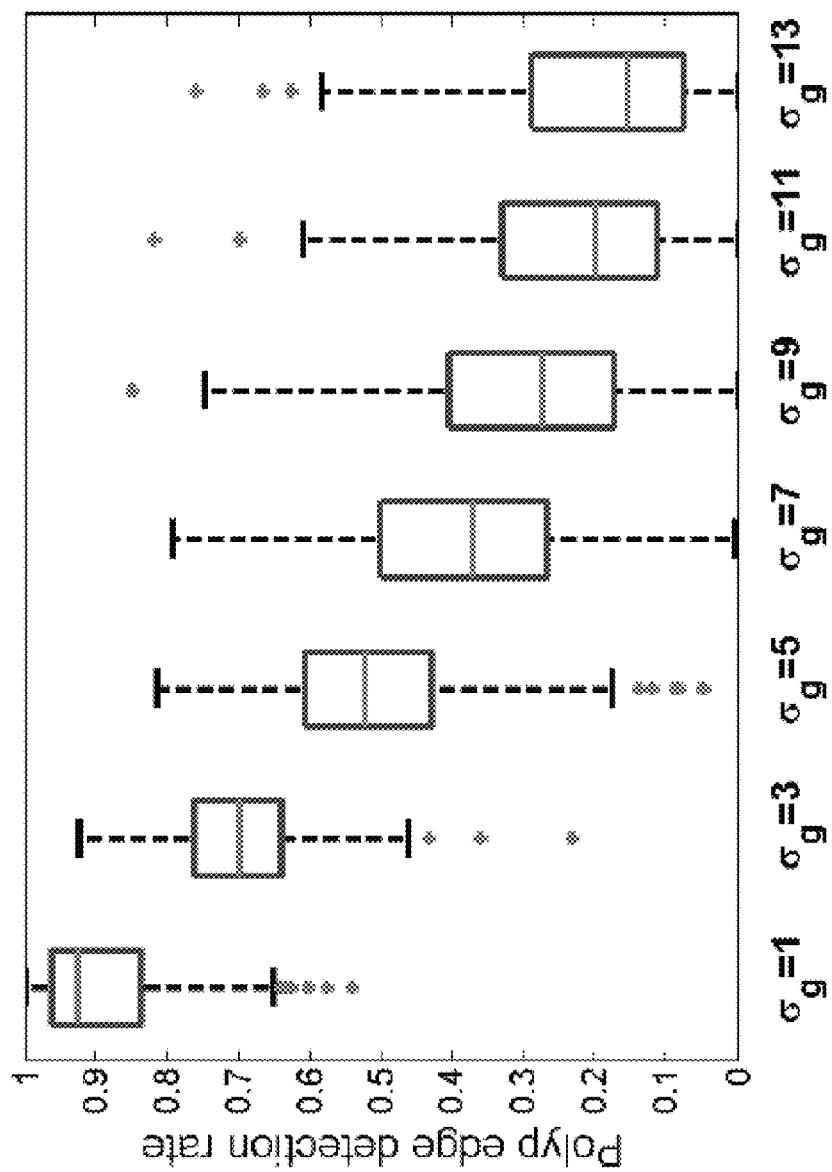
FIG. 13 is a graph showing the effect of Gaussian smoothing on the sensitivity of Canny edge detection.

By way of example, FIG. 12A shows a synthetic shape, its corresponding voting map, and the isocontours for c={0.1, 0.2, 0.4, 0.6, 0.8, 0.9}. As seen, the isocontours become increasingly similar to the original shape as the constant c decreases. This suggests that the isocontours that are farther away from MVA may be more suitable for predicting the actual shape of the object and localizing its underlying edges. However, in practice, such isocontours are not reliable since the tails of vote accumulation may be affected by other nearby voters in the scene. On the other hand, the isocontours that are located very close to MVA do not follow the shape of the object and thus may not be suitable. Therefore, a median shape of a generated set of isocontours may be obtained as the representative isocontour $\bar{\Phi}$ of the voting map (shown in FIG. 12B). Advantageously, the set of isocontours may be chosen so that their corresponding level c uniformly covers the range between 0 and 1. In some aspects, the isocontours may be uniformly selected.

As described, a representative isocontour of a polyp candidate may be used to localize the band skeleton (or polyp boundary). Let $d_{iso}^i$ denote the distance between the $i^{th}$ point on $\bar{\Phi}$ and the candidate location, MVA $d_{iso}^i$ may then be used to predict $d_{obj}^i$, namely the distance between the corresponding point on the object boundary and the MVA within a prediction interval. For this purpose, a second order polynomial regression model may be employed, as follows $$d_{obj}^i = b_0 + b_1(d_{iso}^i) + b_2(d_{iso}^i)^2 \quad (5)$$

where $b_0, b_1$, and $b_2$ are the regression coefficients, which may be estimated using a least square approach. Once the model is constructed, the output of the model $d_{obj}^i$ at angle θ may be taken with respect to MVA as $t_\theta$, and the corresponding prediction interval as the bandwidth δ. With this information, the band can be formed around the polyp candidate and the probability can be computed. A pseudo-code for computing a band around a polyp candidate is shown below.

---

Input:
  A voting map $\mathcal{M}$
  A set of voters $\mathcal{V} = \{v_1, v_2, \ldots, v_n\}$
  A pre-constructed regression model $\mathcal{R}\mathcal{M}$
Output:
  Probability of being a polyp p
Probability computation
  Localize the candidate location (MVA)

MVA ← $\underset{x,y}{\arg\max} \mathcal{M}(x, y)$

Obtain isocontours with respect to MVA
  $\Phi_c = \{(x, y) | V(x, y) = c \times M\}, c \in (0, 1)$
  Compute the representative isocontour
  $\bar{\Phi} = \text{median}(\Phi_c)$
  for θ = 0:359
    Pt ← find the point on $\bar{\Phi}$ at angle θ wrt MVA
    Measure $d_{iso}^\theta = \|\text{MVA} - \text{Pt}\|$
    Apply the regression model $[t_\theta, \delta] = \mathcal{R}\mathcal{M}(d_{iso}^\theta)$
    Form line $l_\theta$ using $t_\theta$, δ
    Search for a voter υ along $l_\theta$
    if (υ with the desired voting direction exists)
      $I_\theta = 1$;

---

-continued else
  $I_\theta = 0$;
end if
end for

Compute probability $p = \frac{1}{180} \sum_{\theta=0}^{179} (I_\theta \vee I_{\theta+180})$

---

In some aspects, a stochastic shape model may be used to perform the voting scheme for a large number of objects. Pairs of $(d_{obj}^i, d_{iso}^i)$ from the boundaries of the synthetic objects may be collected, and along with their representative isocontours may be utilized to build the regression model. In a stochastic shape model, a shape may be parameterized as a curve Γ with the position vector v:

$$\Gamma: \Omega \to \square^2$$

$$\Theta \to v(\Theta) = [x(\Theta), y(\Theta)]^T \quad (6)$$

where $\Theta = \{\theta, \mu_r, \sigma_r, \mu_a, \sigma_a\}$. In the above equation, $x(\Theta)$ and $y(\Theta)$ may be determined as follows:

$$x(\Theta) = C_x + r \times a \times \cos(\theta)$$

$$y(\Theta) = C_y + r \times a \times \sin(\theta) \quad (7)$$

where $C = [C_x, C_y]^T$ is the shape center, θ is the angle with respect to the center, while the radius r and aspect ratio a are drawn from $N(\mu_r, \sigma_r)$ and $N(\mu_a, \sigma_a)$, respectively. Since this model does not pose any constraint on the first and second derivatives of the contours, the resultant shapes are not smooth. To overcome this, the $x(\Theta)$ s of the points on a contour may be concatenated to produce the signal X, and $y(\Theta)$ s to produce the signal Y. A 1D FFT may then be applied on the generated signals to remove the high frequency components, and signals $\hat{X}$ and $\hat{Y}$ can then be reconstructed using the remaining low frequency coefficients. To compensate for unwanted shrinking caused by the smoothing process, the smoothed shapes may be scaled up to the original size using the following linear transformation:

$$x(\Theta) = C_x + (\hat{x}(\Theta) - C_x) \frac{\sum_i X_i}{\sum_i \hat{X}_i} \quad (8)$$

$$y(\Theta) = C_y + (\hat{y}(\Theta) - C_y) \frac{\sum_i Y_i}{\sum_i \hat{Y}_i}$$

The regression model defined in Eqn. 5 is a function of the representative isocontour, which itself is a function of the voting scheme. As a result, one can obtain different regression models for different configurations.

In some aspects, to find the best model, an initial set of regression functions may be constructed using different values of K and $\sigma_F$. For this purpose, the synthetic shapes generated by a shape model may be used because it allows for experimenting with a large number of curvy objects, keeping the derived models generalizable rather than specific to shape variations among a small set of real polyps. The initial set of regression models may then be narrowed down by experimenting with the synthetic shapes and finding the best value of K. The polyp detection results may also be used to find $\sigma_F$ and select the best regression model.

By way of example, the following steps can be taken. First, a number of objects, for instance, 3000, may be generated at three different scales corresponding to small, medium, and large polyps. To do so, a shape generator model can be used, and, for instance, choosing $\mu_r \in \{20, 40, 60\}$, and setting $\sigma_r = 0.2\ \mu_r$, $\mu_a = 1$ and $\sigma_a = 0.1$. Second, a voting scheme may be performed for each generated object using $K \in \{2,3,4,5,6\}$ and $\sigma_F \in \{60,70,80,90,100\}$. The set of voters consists of all the edge pixels that form the object contour. To initiate the voting process, each voter must be assigned a voting direction. As described, the edge direction for an edge pixel may be obtained using ball tensor voting, with its voting direction determined such that it points towards inside the corresponding object. Third, representative isocontours of the generated voting maps is found, with pairs of $(d_{obj}^i, d_{iso}^i)$ collected from the boundaries of the objects and the representative isocontours. Fourth, a regression model based on the collected pairs is built for each configuration of the parameters and then model fitness is evaluated. Table 1 shows the $R^2$ coefficient for the constructed regression models.

TABLE 1

$R^2$ coefficients for regression models constructed under different configurations of the present voting scheme.

| | | Size of the voting field | | | | |
|---|---|---|---|---|---|---|
| | | $\sigma_F = 60$ | $\sigma_F = 70$ | $\sigma_F = 80$ | $\sigma_F = 90$ | $\sigma_F = 100$ |
| # voting groups | K = 2 | 0.863 | 0.905 | 0.921 | 0.928 | 0.928 |
| | K = 3 | 0.830 | 0.890 | 0.916 | 0.930 | 0.936 |
| | K = 4 | 0.820 | 0.891 | 0.924 | 0.941 | 0.951 |
| | K = 5 | 0.812 | 0.889 | 0.923 | 0.941 | 0.950 |
| | K = 6 | 0.794 | 0.876 | 0.914 | 0.934 | 0.946 |

The coefficient of determination, or $R^2$, indicates how well the data fit into a statistical model. The higher the $R^2$, the better the fit. If the model explains all the variation in the data, $R^2$ will reach a maximum of 1. As seen, model fitness or the ability to localize object contours initially increases but then decreases as the number of voting categories increases. This is because too few voting categories results in large angle quantization error and thus the shapes of the representative isocontours do not follow the shape of the object. On the other hand, too many quantization level favor pure circular objects, limiting the localization capability for objects that deviate from a complete circle. As such, in some aspects, K may taken on a value of 4, although other values could be possible. Model fitness, however, monotonically increases as the size of the voting fields increases. This is because the parts of the boundaries that are farther away from the object centers need larger voting fields in order to contribute to vote accumulation. However, in practice, $\sigma_F$ might not be set to an arbitrary large value since it causes voting interference from the voters lying on the other nearby objects and also induce a heavy computational burden.

In addition to descriptions above, specific examples are provided below, in accordance with the present disclosure. These examples are offered for illustrative purposes only, and are not intended to limit the scope of the present invention in any way. Indeed, various modifications in addition to those shown and described herein will become apparent to those skilled in the art from the foregoing description and the following example and fall within the scope of the appended claims.

EXAMPLE

To evaluate the approach of the present disclosure, image data from CVC-ColonDB database in the form of 300 colonoscopy images with 20 pedunculated polyps, 180 sessile polyps, and 100 flat polyps. These were collected from 15 short colonoscopy videos such that maximum variation in scale and view angles were captured.

1. Edge Detection: Edge detection yields a crude set of candidate edges. The lower and upper thresholds of the Canny were computed automatically relative to the highest value of the gradient magnitude of the images. To determine the degree of Gaussian smoothing, $\sigma_g$, a set of experiments was performed to investigate how changes in Gaussian smoothing can affect the percentage of polyp edges that can be detected by the Canny in each of the 300 images. To measure the percentage of polyp edges detected by the Canny, the resulting edge maps were compared against the ground truth for polyps. To do so, for each boundary pixel in the ground truth, the closest edge pixel from the edge map was found. If the minimum distance as less than 10 pixels, that polyp boundary pixel was marked as detected. Note that due to Gaussian smoothing before applying the Canny, some degrees of edge mis-localization was present. Once all the polyp boundary pixels were labeled, the polyp edge detection rate was measured. The edge detection results are shown in FIG. 12 where each box plot displays the distribution of polyp edge detection rates for the 300 images. As seen, the Canny edge detector can effectively capture a high percentage of polyp edges particularly for the small values of $\sigma_g$. The red crosses below the box plots correspond to the polyps having faint edge segments in their boundaries. For instance, some polyps had almost no recognizable boundary where attached to the colon wall. For such polyps, a low edge detection rate was obtained, because the corresponding ground truth included such a low gradient region as a part of the polyp boundary.

2. Feature Extraction: For feature evaluation, 50,000 oriented patches were collected around polyp and other boundaries in colonoscopy images. The polyp patches are collected so that the polyps always appeared on the right side of the image patches. That is, the patches that had polyp regions on their left sides were not included. This resulted in a binary classification problem, which can simply be evaluated using ROC curves. Half of the image were selected from training, and the rest were used for testing. For classification, a random forest classifier was used. Experiments with the training set revealed that selecting 8×16 sub-patches in each image patch and extracting 3 DCT coefficients from each sub-patch yielded a good balance between the size of feature vectors and the discrimination power. This configuration resulted in a feature vector with 315 elements for each image patch. Evaluations demonstrated that choosing more than 3 coefficients did not achieve any significant improvement in classification performance.

Figure 14:
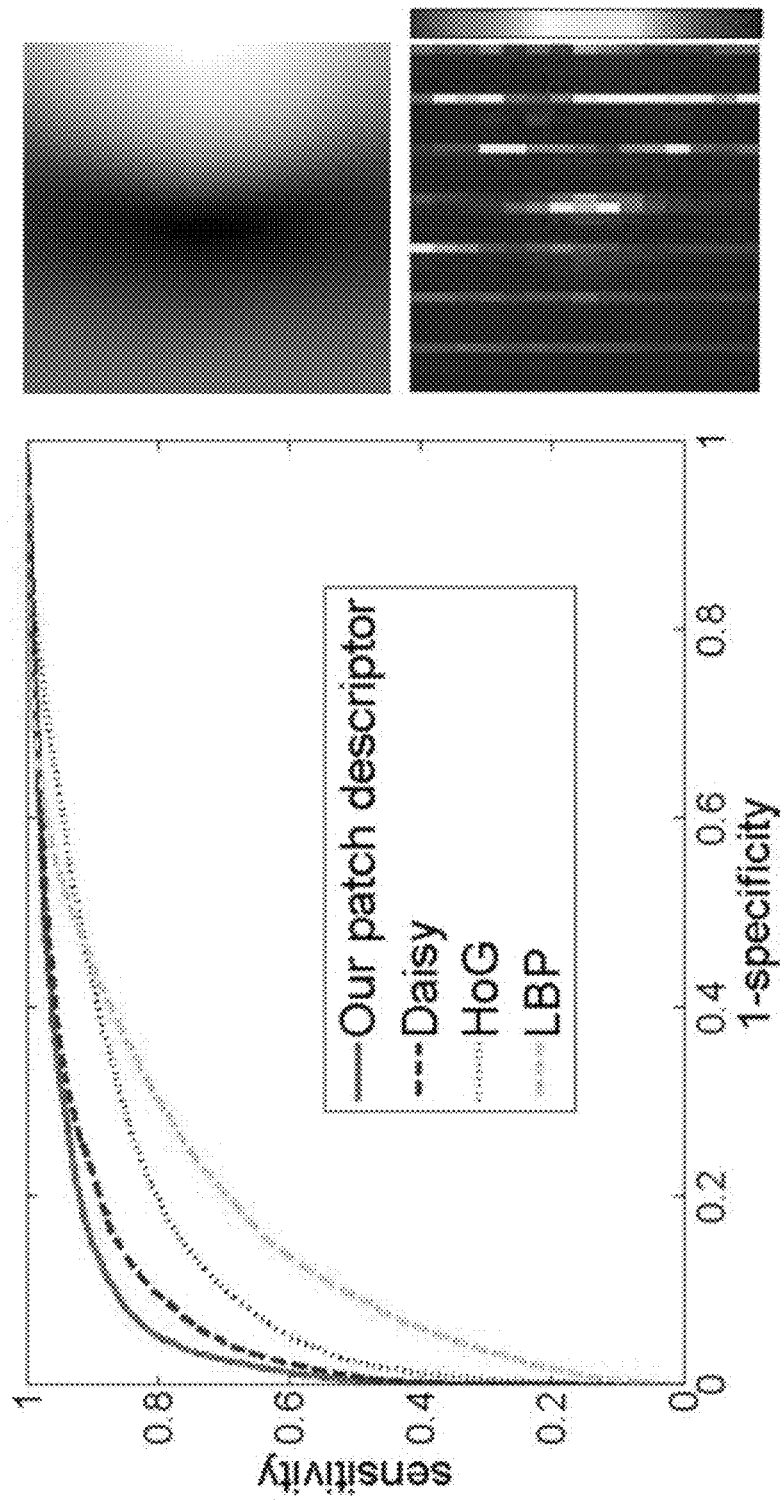
FIG. 14 is a graphical illustration comparing a patch descriptor, in accordance with aspects of the present disclosure, with those utilized by prior techniques.

For comparison, other widely-used patch descriptors, such as HoG, LBP, and Daisy were used after being tuned on the training set. For LBP, histograms of the uniform patterns at 3 radii (r=1,2,3 pixels) were computed and concatenated. For HoG, cells of size 8×8 pixels were used, along with blocks of size 2×2 cells or 16×16 pixels. A gradient histogram was computed with 9 orientation bins in each block and then concatenated the resulting histograms. For Daisy, three concentric rings were defined around the center of the patch and then 8 equally spaced points were selected on each ring. Next, 8-bin gradient histograms computed at each of the selected points were concatenated. FIG. 14 shows the ROC curve for the present patch descriptor when applied on the test set in comparison to these previous approaches. As seen, the present descriptor surpasses HOG and LBP with a large margin and outperforms Daisy with a small yet statistically significant margin (p<0.0001).

To further analyze the extracted features, the variable importance computed by the random forest classifier was visualized for each of the extracted features. The random forest calculated the variable importance for feature $f_i$ in each tree and then took their average to compute the overall importance of feature $f_i$. To measure the importance of feature $f_i$ in each tree, the random forest classifier permuted the values of this feature in the out-of-bag samples randomly, and then measured the subsequent decrease in the classification performance. A feature was considered important if the corresponding permutations minimally affected classification performance. The variable importance of all the 315 features was collected and then reshaped them into a matrix form such that each feature was mapped to the part from which it had been extracted. To visually compare the importance map with the average of polyp patches (shown in FIG. 14), this matrix was scaled up to the same size as the input image patches, as shown in FIG. 14. As seen, while the discriminative patterns are found all over the patches, they were more densely located inside the polyp region and across the polyp boundary. The relatively less number of important features on the background side (left side) of the patches can be explained by the large variability in the backgrounds of polyps. 100971 On a desktop computer with a 2.4 GHz quad core 64×64 image patches were processed at 36,000 frames/sec. Considering that the edge map of a colonoscopy image after applying Gaussian smoothing contains on average 20,000 edge pixels, the present descriptor was able to process all the resulting patches in approximately 0.5 seconds. A significant performance speed-up is expected using multi-core parallel computing or GPU programming.

3. Edge Classification: A 5-fold cross validation was used to train the 2-stage classification system. In particular, to train the first classification layer, $N_1=100,000$ oriented image patches were collected from each training fold, with almost 20,000 samples for each of the five chosen structures. To train the second classification layer, $N_2=100,000$ pairs of oriented image patches were also collected, where half of the pairs were extracted around polyps and the rest around edges in random locations in the training images. For classification, a random forest classifier was chosen, which has been successfully applied to a variety of computer vision and medical image analysis applications, outperforming other widely-used classifiers, such as AdaBoost and support vector machines. The two main ingredients of random forest include bagging of a large number of fully grown decision trees and random feature selection at each node while training the trees, which together achieve low generalization error and high quality probabilistic outputs. In the present experiments, adding decision trees to the random forest classifier were kept until the decreasing trend of out-of-bag error converged. It turned out that using 100 fully grown decision trees achieved a stable out-of-bag error for both random forest classifiers.

4. Voting Scheme: The described voting scheme has two parameters, namely the size of voting fields $\sigma_F$ and the number of voting categories K. As described, it was experimentally determined that that K=4 can achieve the best boundary localization for synthetic objects. However, the impact of $\sigma_F$ was not studied since the synthetic objects generated by the shape model did not simulate the effects of nearby voters on boundary localization. As such, the impact of $\sigma_F$ on the accuracy of polyp detection was hence examined in real colonoscopy images. For this purpose, the regression models, constructed as described above, were used, and the sensitivity of polyp detection was compared at 0.05 false positives per image. The results are summarized in Table II.

TABLE 2

Sensitivity of polyp detection at 5% false positive per image for different amounts of Gaussian smoothing and sizes of voting fields.

| | | Size of the voting field | | | | |
|---|---|---|---|---|---|---|
| | | $\sigma_F = 70$ | $\sigma_F = 80$ | $\sigma_F = 90$ | $\sigma_F = 100$ | $\sigma_F = 110$ |
| Edge smoothing | $\sigma_g = 1$ | 72% | 71% | 69% | 66% | 67% |
| | $\sigma_g = 2$ | 80% | 77% | 73% | 72% | 71% |
| | $\sigma_g = 3$ | 79% | 81% | 78% | 77% | 77% |
| | $\sigma_g = 5$ | 70% | 69% | 73% | 72% | 68% |
| | $\sigma_g = 7$ | 44% | 40% | 49% | 56% | 48% |

As seen in Table 2, stable results were achieved for a wide range of $\sigma_F$ values, with the best result using $\sigma_F=80$. In general, smaller values of $\sigma_F$ enable the detection of polyps that "appear" small in the colonoscopic view, and large values of $\sigma_F$ are suitable for detecting the polyps that "appear" large in the colonoscopic view. Note that the physical size of polyps may differ from what appears in the videos because the former is fixed but the latter varies depending on the distance between the polyp and the camera. According to the experiments, the optimal value of $\sigma_F$ can be generalizable to the collected videos used, and is suitable for detecting the polyps that appear small or moderate in the colonoscopic view. In practice, polyps that appear large in the videos would be likely already detected and under examination by colonoscopists, and as such not requiring computer-aided polyp detection. In fact, choosing $\sigma_F$ for detecting polyps that appear large in the videos would not only have limited clinical value but also decrease the probability of success for polyps that appear small because large voting fields open the door for voting interference from the voters that are located on the boundaries of nearby objects.

Figure 15:
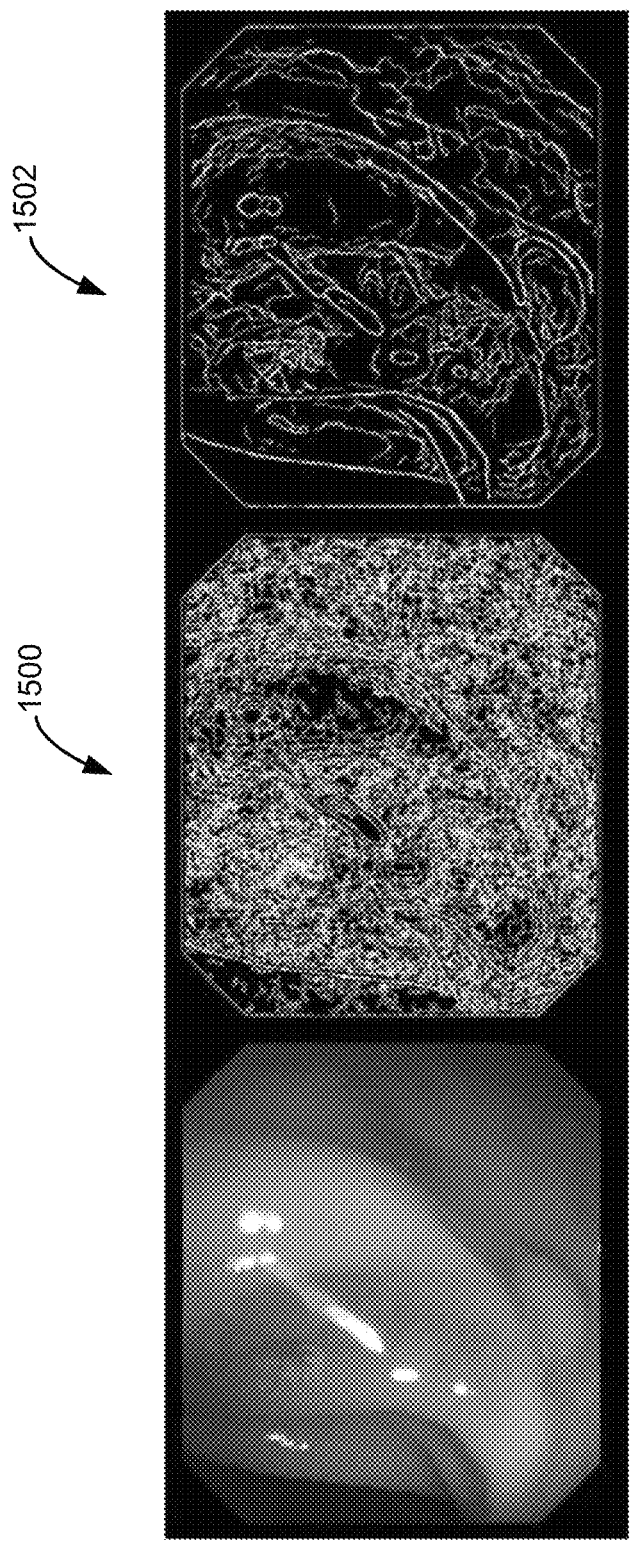
FIG. 15 shows generated edge maps of an example optical image, generated in approach in accordance with the present disclosure.

From Table 2, it may be observed that $\sigma_g=3$ yielded the highest sensitivity to polyps. As shown in the example of FIG. 15, lower performance for smaller values of $\sigma_g$ was attributed to over-cluttered edge maps 1500 that cause unreliable edge orientation estimation, while poor performance for larger values was attributed to aggressive edge removal, and hence more sparse maps 1502, due to heavy Gaussian smoothing. Optimal values of $\sigma_g$ and $\sigma_F$ were used for the subsequent evaluations.

Figure 16:
FIG. 16 shows optical images highlighting identified polyps using an approach in accordance with the present disclosure.
Figure 17:
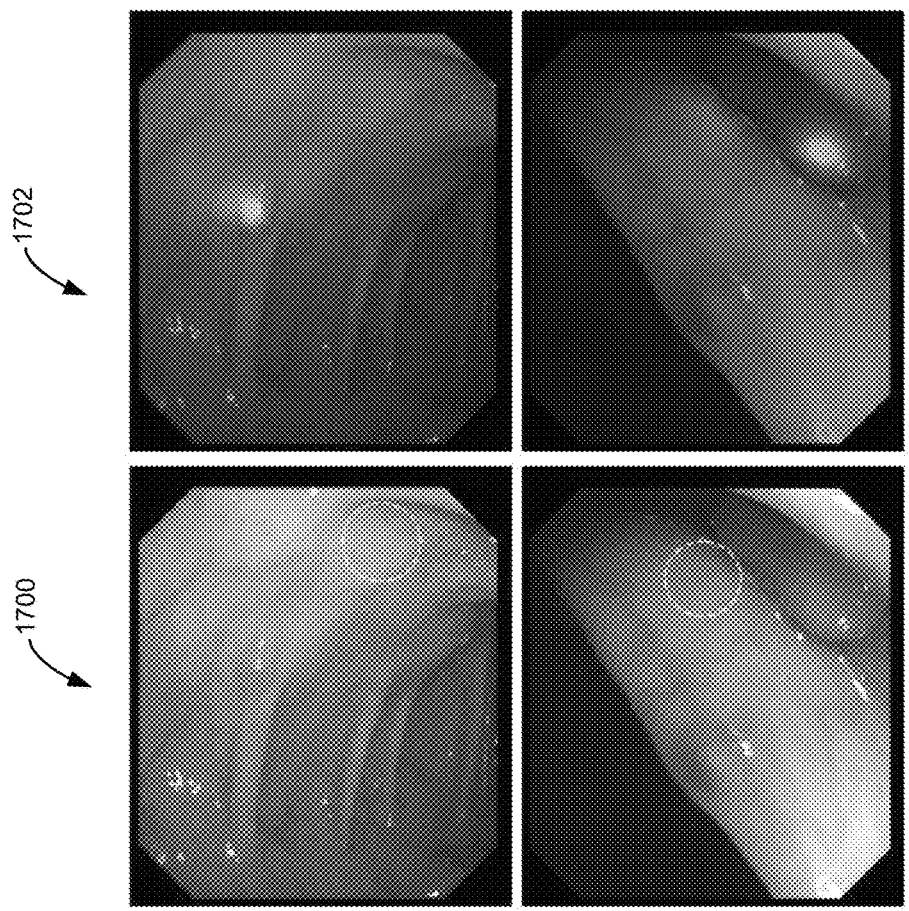
FIG. 17 shows optical images comparing the present polyp detection approach to a prior art technique.

FIG. 16 shows examples of successful polyp localizations from CVC-ColonDB when $\sigma_g=3$, $\sigma_F=80$, and K=4 were used. For better visualization, the voting heat maps are superimposed on the original images, showing only a number of the constituent line segments of the discrete bands. A color coding was used to indicate the line segments that hit at least a voter with the desired voting direction (blue), as well as those line segment that did not hit at least one voter with the desired voting direction (red), indicated in FIG. 16 with labels 1600 and 1602, respectively. As appreciated from FIG. 16, the present polyp detection approach was able to localize polyps of different shapes, scales, and colors.

To demonstrate the effectiveness of the described voting scheme, a performance comparison with the phase based Hough transform is shown in terms of polyp detection accuracy, boundary localization accuracy, and the quality of scores assigned to polyp candidates. Specifically, to measure polyp detection accuracy, both algorithms were applied on the same refined edge maps. The radius range of the Hough transform was tuned to detect the smallest and biggest polyps in the images. Evaluations revealed that the Hough transform placed the polyp candidates inside of the 300 polyps, which was outperformed by the present voting scheme with 262 out of 300 polyps. FIG. 16 shows examples where the Hough transform fails to localize polyps, while the present voting scheme correctly places the candidates inside the polyps, indicated in FIG. 16 using labels 1700 and 1702, respectively.

Figure 18:
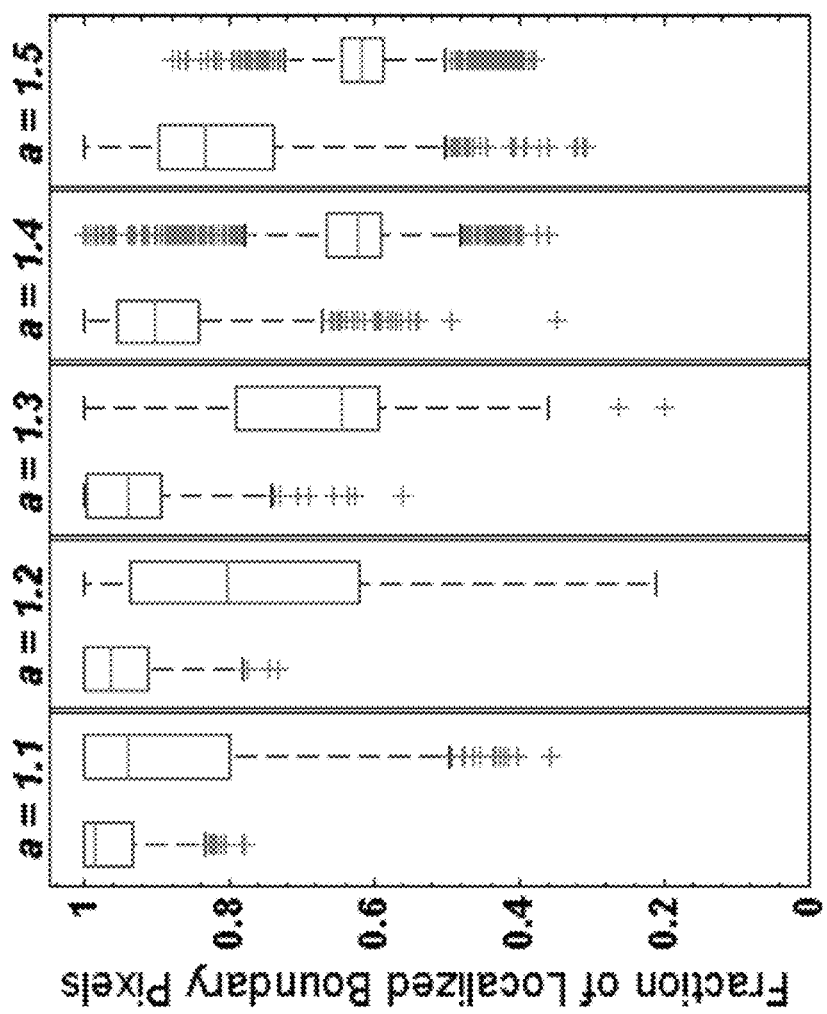
FIG. 18 is a graphical illustration comparing the boundary localization of a voting scheme, in accordance with the present disclosure, and that of a Hough transform.

To compare boundary localization accuracy of the present voting scheme with that of the Hough transform, shapes with varying level of deviation from a complete circle were generated. Measurements were made regarding what percentages of boundary pixels fell inside the bands (estimated by the present voting scheme) and percentages of boundary pixels that fell inside the bands that placed around the circles estimated by the Hough transform. For fair comparisons, bands of the same width were for both algorithms. Deviation from a complete circle was injected by increasing the aspect ratio. FIG. 18 compares the boundary localization of the present voting scheme with that of the Hough transform. In each subplot, the left box plot corresponds to the present voting scheme and the right box plot corresponds to the Hough transform. As seen, the present voting scheme localizes boundary pixels more accurately than the Hough transform.

Figure 19:
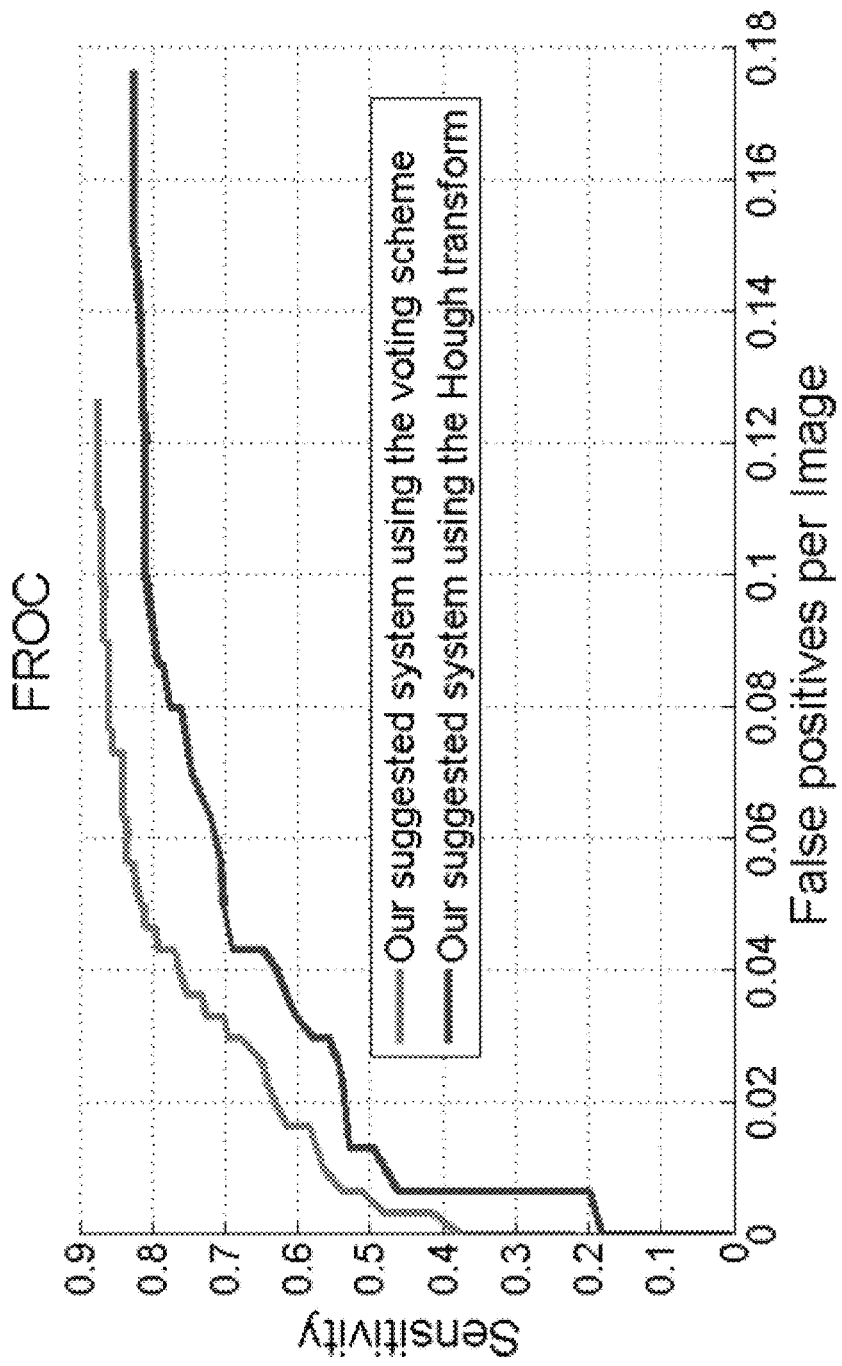
FIG. 19 is a graph comparing the sensitivity of a voting scheme, in accordance with the present disclosure, and that of a Hough transform.

To evaluate the scores assigned to each polyp candidate by the present voting scheme in comparison to the Hough transform, an Free-response Receiver Operating Characteristic (FROC) analysis was performed. For this purpose, a threshold on the collected scores was changed and then the sensitivity and the number of false positives was computed at each threshold. As shown in FIG. 19, the present voting scheme significantly outperformed the Hough transform in all the operating points.

5. Performance Comparison: Comparisons in the precision and recall rates of the present method with to those previously reported were performed using VC-ColonDB. Results showed that the present method outperformed previous methods with a large margin, and also improved the precision of work published by the present group. It is important to note that the present polyp detection criterion was more strict than the one used by Bernal et al. A polyp was considered as "detected" if the polyp candidate fell inside the ground truth. On the other hand, Bernal et al. used a region-based approach that did not require the polyp candidates to fall inside the provided truth.

Figure 20:
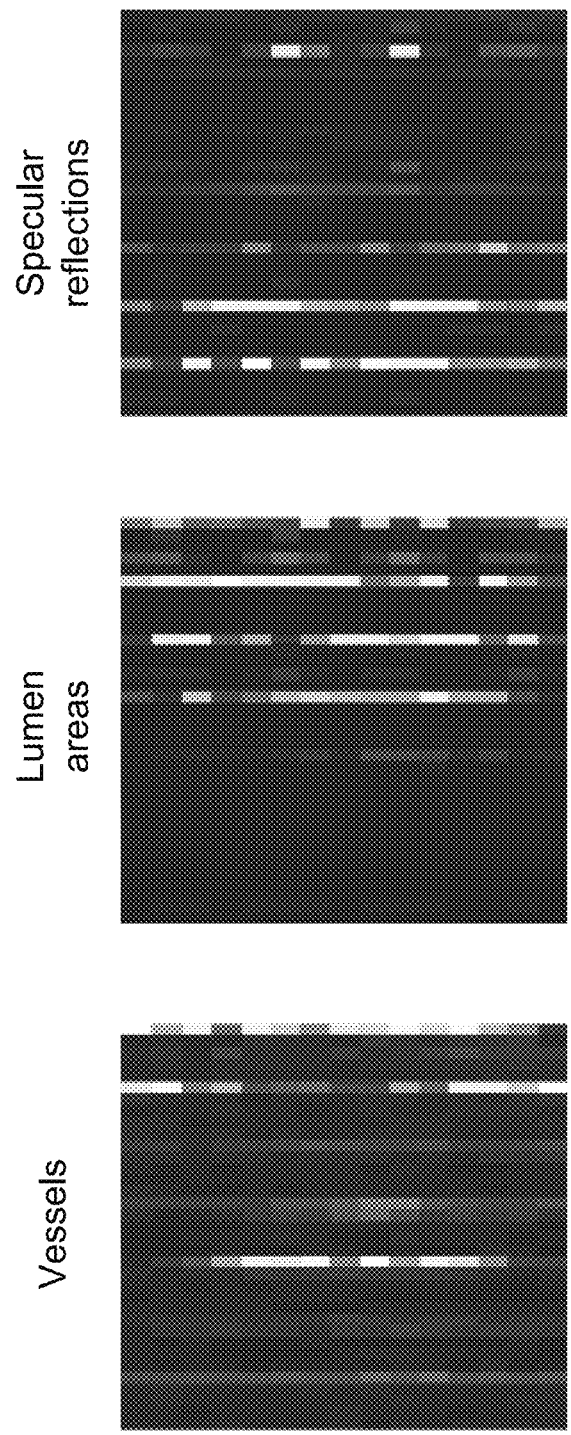
FIG. 20 shows variable importance maps discriminating polyps against vessels, lumen areas, and specular reflections.

Theoretically, a system, in according to the present exposure, is also expected to outperform the work of Bernal et al. To clarify this, binary classifiers for vessel vs. polyps, lumen areas vs. polyps, and specular reflections vs. polyps were trained. Similarly, oriented patches were used such that the structure of interest appeared on right side of the patches and the background on the left side of the patches. Variable importance maps were then obtained for each classification scenario (shown in FIG. 20). Bernal et al. used the valley information for polyp localization, which corresponds to the information that the middle parts of the oriented patches. However, as seen in FIG. 20, features from other parts of the patches were equally or even more important for discriminating polyps against vessels, specular reflections, and lumen areas. Relying on only the central features resulted in much weaker discrimination power. Furthermore, their work assumes polyps as circular structures whose radii vary in a pre-specified range. Herein, no prior shape models for polyps were assumed, and the scales of polyps were estimated automatically using the pre-constructed regression models.

Figure 21:
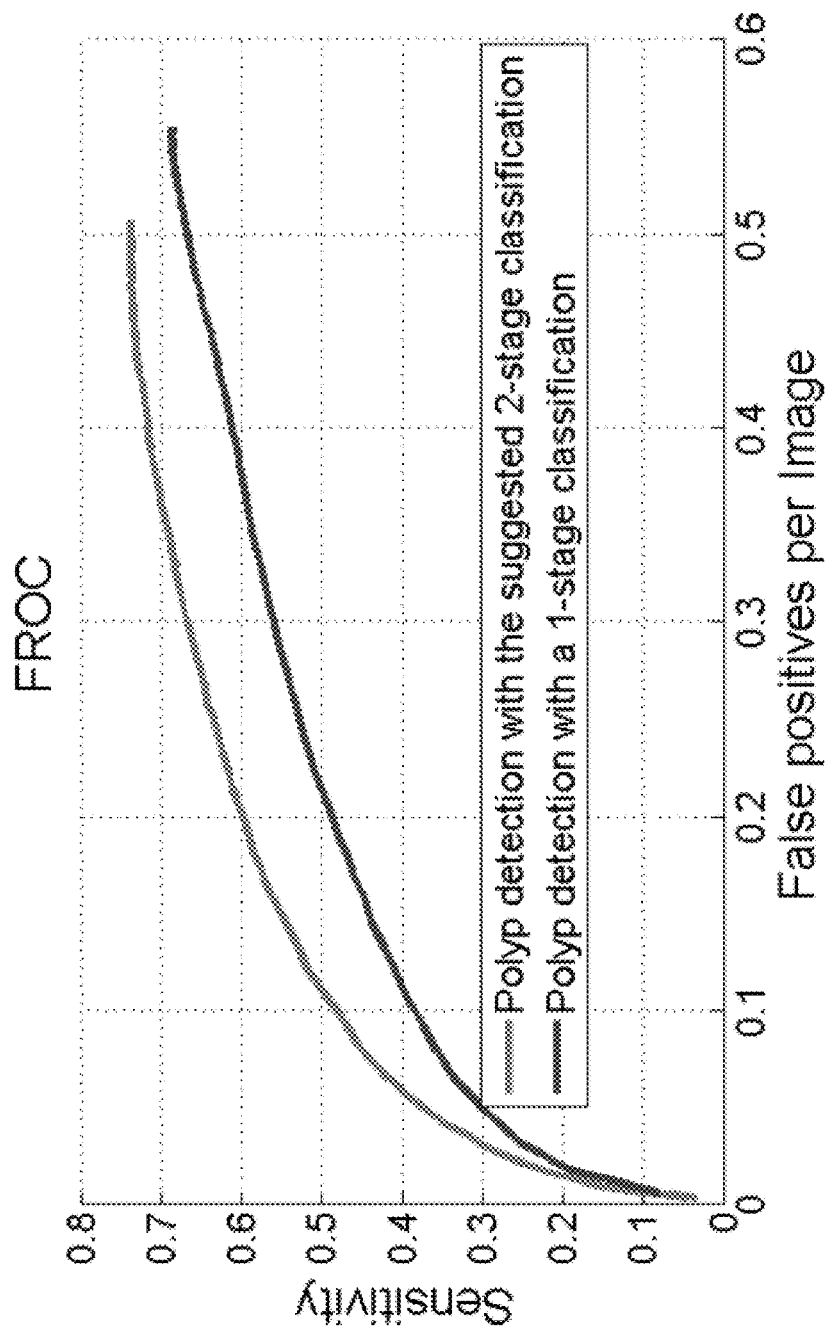
FIG. 21 is a graph comparing a single stage classification and a two-stage classification in accordance with aspects of the present disclosure.

The present polyp detection system was also evaluated using 12 short colonoscopy videos from a database, comprising 5800 images with polyps and 3075 images without polyps. The ground truth was manually created for each frame in the videos that contained a polyp, a tedious and time-consuming task resulting in 5800 ground truth images. For evaluation, the classification system was trained on the entire CVC-ColonDB and previously tuned parameters $\sigma_g=3$, $\sigma_F=80$, and $K=4$ were used. The free ROC curve of the present approach is shown in FIG. 21. For comparison, the the performance of a 1-stage classification scenario is also shown, where a binary random forest classifier was employed. To enable polyp detection in this scenario, a pair of patches was extracted around each edge pixel, followed by application of the binary classifier on the pair of patches. The classification was then performed according to the larger score of the two patches. The normal vector associated with the patch of higher score was selected as the voting direction for the underlying edge pixel. As explained above and shown in FIG. 21, the second classification layer is superior for achieving accurate edge classification, without which a significant drop in polyp detection performance is observed.

In descriptions above, a system that detects colonic polyps in colonoscopy videos was presented. The system was tested on 2 polyp databases: (1) a public polyp database, CVC-ColonDB, and (2) a database consisting of a collection of acquired colonoscopy videos. The performance of the present system was evaluated by FROC analysis. At 0.05 false positive per image, a sensitivity of 0.81 for detecting polyps in CVC-ColonDB and 0.40 for the collection of colonoscopy videos was obtained. The performance variation between these two databases can be explained by the insufficient number of images in CVC-ColonDB. The absence of images with no polyps the CVC-ColoDB database prevented the solid evaluation in terms of false positive rate. This limitation was compensated in the second database by including a large number of frames without colonic polyps.

For a polyp detection system to be used clinically, an operating point has to be chosen at which the number of false positives is acceptable for clinicians. When choosing such a threshold, one should consider that a detection system need not achieve perfect sensitivity to be clinically useful, since a polyp usually appears in several consecutive frames and if one instance of the polyp—particularly upon appearance—gets detected, the detection process is considered as a success. This may allow for moving the operating point to the left on the FROC curve where a significant reduction in the number false positives is achieved.

Polyps missed by the provided system may have occurred due to partial edge detection and unsuccessful edge classification. The former occurs for polyps that are surrounded by low gradient boundaries. Such weak edges are not detected during edge detection and cannot be recovered in the subsequent edge classification stage. A polyp with an incomplete boundary may appear as a non-curvy structure and thus might not be detected in the voting stage. Other polyp mis-detection, or unsuccessful edge classification, might occurs when the desired intensity variation patterns are not observed around the polyp boundaries. Image degradation factors such as interlacing artifacts, motion blurriness, and boundary occlusion can corrupt the intensity variation patterns around the boundaries, resulting in misclassification of the underlying edge pixels. Similarly, a polyp with a large number of misclassified edges cannot be detected in the voting scheme.

The described system processes each colonoscopy image at 2.6 seconds on average, which is significantly less than previous approaches, with run-time greater than 7 seconds. By converting a Matlab-Mex implementation to C/C++ and employing parallel computing optimization, real time processing for live colonoscopy procedures is expected. IN addition, the present system could also be used for detecting polyps in capsule endoscopy images. In contrast to optical colonoscopy, capsule endoscopy is not a live process so a system, as described, could be employed in an off-line fashion to scan the images for polyps or other types of lesions in the gastrointestinal tracts. In another application, the described system could be used to annotate stored colonoscopy videos in a post-exam setting. Such a video annotation mechanism in conjunction with other quality documentation systems can be used for more effective colonoscopy reimbursement.

In summary, a system and methods implementing a novel polyp detection approach, with performance superior to the state-of-the-art, and achieving a suitable level of sensitivity and specificity, are provided. Specifically, the present approach first identifies a set of edge pixels, forming one or more edge maps constructed from provided or acquired optical images. The set of edge pixels is then refined by effectively removing non-polyp boundary edges through a novel classification scheme. The retained edges vote along voting directions determined by a classifier, and a band is placed around each candidate point with maximum vote to measure a polyp probability. In this manner, misleading effects of polyp-like structures are avoided, facilitating a robust polyp localization.

The approach of the present invention was demonstrated capable of detecting polyps using collected image data as well as data found in a public database. Noteworthy, the suggested boundary classification framework, in accordance with aspects of the present invention, is general and can be applied to a variety of medical segmentation problems where a supervised edge classification can serve as a pre-processing stage prior to segmentation. In addition, an important consideration is computer aided detection for colonoscopy need not to achieve perfect sensitivity to be clinically useful, because a polyp usually appears in a number of consecutive frames and if one instance of the polyp—particularly upon appearance—is detected, the detection process may be considered successful.

The present invention has been described in terms of one or more preferred embodiments, and it should be appreciated that many equivalents, alternatives, variations, and modifications, aside from those expressly stated, are possible and within the scope of the invention.

What is claimed is:

1. A system for identifying polyps using optical colonoscopy images, the system comprising:
   an input configured to receive a series of optical images acquired from a subject using an imaging system;
   a processor configured to process the series of optical images with steps comprising:
   i. receiving an optical image from the input;
   ii. constructing an edge map having a plurality of edge pixels using the optical image;
   iii. classifying each of the plurality of edge pixels in the edge map based on patterns of intensity variation determined using the optical image;
   iv. generating a refined edge map based on the classification at step iii);
   v. analyzing the refined edge map to identify polyps;
   vi. generating a report indicating polyps identified; and
   an output for displaying the report.

2. The system of claim 1, wherein the processor is further configured to separate the optical image into color channels and apply a Canny technique to the color channels to construct the edge map.

3. The system of claim 1, wherein the processor is further configured to generate an orientation map corresponding to the edge map constructed.

4. The system of claim 3, wherein the processor is further configured to apply a tensor voting technique to construct the orientation map.

5. The system of claim 1, wherein the processor is further configured to generate image patches for each of the plurality of edge pixels, wherein each image patch is oriented such that a corresponding edge segment appears vertically approximately in the middle of the image patch.

6. The system of claim 5, wherein the processor is further configured to generate pairs of oriented patches using the image patches generated for each of the plurality of edge pixels.

7. The system of claim 6, wherein the processor is further configured to classify, based on the appearance of the pairs of oriented patches, selected edges associated with the plurality of edge pixels as corresponding to an object category.

8. The system of claim 7, wherein the object category includes a polyp, a vessel, a lumen, and a specular reflection.

9. The system of claim 1, wherein the processor is further configured to perform a voting scheme using the refined edge map to identify polyps.

10. The system of claim 1, wherein the processor is further configured to compute probabilities for the polyps identified by generating a band around each polyp consisting of radial line segments whose extensions pass through the polyps.

11. A method for identifying polyps from optical colonoscopy images, the method comprising:
    receiving an optical image acquired from a subject using an imaging system;
    constructing an edge map corresponding to the optical image, the edge map comprising a plurality of edge pixels;
    generating a refined edge map by applying a classification scheme, based on patterns of intensity variation, to the plurality of edge pixels in the edge map;
    identifying polyp candidates using the refined edge map;
    computing probabilities that identified polyp candidates are polyps; and
    generating a report, using the computed probabilities, indicating detected polyps.

12. The method of claim 11, wherein the method further comprises applying a Canny technique to multiple color channels determined using the optical image.

13. The method of claim 11 wherein the method further comprises generating an orientation map corresponding to the constructed edge map.

14. The method of claim 13, wherein the method further comprises applying a tensor voting technique to generate the orientation map.

15. The method of claim 11, wherein the method further comprises performing a feature extraction by identifying the patterns of intensity variation in image patches corresponding to respective ones of the plurality of edge pixels.

16. The method of claim 11, wherein the method further comprises performing an edge classification by analyzing a pair of oriented patches corresponding to each of the plurality of edge pixels.

17. The method of claim 16, wherein the method further comprises determining, based on the appearance of the pair of oriented patches, a classification of respective one of the plurality of edge pixels as corresponding to an object category.

18. The method of claim 17, wherein the object category includes a polyp, a vessel, a lumen, and a specular reflection.

19. The method of claim 11, wherein the method further comprises performing a voting scheme using the refined edge map to identify the polyp candidates.

20. The method of claim 11, wherein computing the probabilities includes generating a band around identified polyp candidates consisting of radial line segments whose extensions pass through a polyp candidate location.

* * * * *